(12) United States Patent
Nelson et al.

(10) Patent No.: US 8,361,712 B2
(45) Date of Patent: Jan. 29, 2013

(54) CONTAMINATION-FREE REAGENTS FOR NUCLEIC ACID AMPLIFICATION

(75) Inventors: John Richard Nelson, Clifton Park, NY (US); Robert Scott Duthie, Schenectady, NY (US); Gregory Andrew Grossmann, Halfmoon, NY (US)

(73) Assignee: General Electric Company, Niskayuna, NY (US)

( * ) Notice: Subject to any disclaimer, the term of this patent is extended or adjusted under 35 U.S.C. 154(b) by 434 days.

(21) Appl. No.: 11/957,534

(22) Filed: Dec. 17, 2007

(65) Prior Publication Data
US 2009/0155859 A1 Jun. 18, 2009

(51) Int. Cl.
*C12Q 1/68* (2006.01)
*C12P 19/34* (2006.01)

(52) U.S. Cl. .................. 435/6.1; 435/91.2
(58) Field of Classification Search .................. None
See application file for complete search history.

(56) References Cited

U.S. PATENT DOCUMENTS

| | | | |
|---|---|---|---|
| 5,516,292 A | 5/1996 | Steinman | |
| 6,541,204 B2 | 4/2003 | Nilsen et al. | |
| 2002/0172972 A1 | 11/2002 | Tabor et al. | |
| 2004/0248105 A1 | 12/2004 | Kumar | |
| 2005/0037349 A1* | 2/2005 | Picard et al. | 435/6 |
| 2005/0084863 A1 | 4/2005 | Price | |

FOREIGN PATENT DOCUMENTS

| | | |
|---|---|---|
| EP | 0744470 A1 | 11/1996 |
| EP | 0585660 B1 | 5/2000 |
| JP | 2004057055 A | 2/2004 |
| WO | 03070986 A | 8/2003 |
| WO | 03087402 A | 10/2003 |
| WO | 03102243 A1 | 12/2003 |
| WO | 2004020604 A | 3/2004 |
| WO | 2007105965 A | 9/2007 |

OTHER PUBLICATIONS

Corless et al. Contamination and sensitivity issues with a real-time universal 16S rRNA PCR. J. Clinical Microbiology (2000) vol. 38, No. 5, pp. 1747-1752.*
Zhu et al.; The use of exonuclease III for polymerase chain reaction sterilization; Nucleic Acids Research, vol. 19, No. 9 2511, 1 page, (1991).
Meier Albrecht et al., "Elimination of contaminating DNA within polymerase chain reaction reagents: Implications for a general approach to detection of uncultured pathogens" Journal of Clinical Microbiology, vol. 31, No. 3, 1993, pp. 646-652.
Hughes M S et al., "Identification and elimination of DNA sequences in Taq DNA polymerase" Journal of Clinical Microbiology, vol. 31, No. 8, 1994, pp. 2007-2008.
Goto M et al., "Contamination of diverse nifH and nifH-like DNA into commercial PCR primers" FEMS Microbiology Letters, Amsterdam, NL, vol. 246, No. 1, May 1, 2005, pp. 33-38.
Search report and Written Opinion from PCT Application No. PCT/EP2008/067259 dated Jun. 22, 2010.

* cited by examiner

Primary Examiner — Kenneth R. Horlick
Assistant Examiner — David Thomas
(74) Attorney, Agent, or Firm — Jenifer Haeckl

(57) ABSTRACT

Methods and kits for generating contamination-free reagents and reagent solutions for use in nucleic acid amplification are provided. Methods include processing of polymerase solutions, nucleotide solutions and primer solutions to render contaminating nucleic acid inert. The methods employ the proofreading activity of the polymerase and/or exonucleases to de-contaminate the reagents and reagent solutions. Methods and kits for contamination-free nucleic acid amplification are provided.

16 Claims, 11 Drawing Sheets

CONTAMINATION-FREE REAGENTS FOR NUCLEIC ACID AMPLIFICATION

BACKGROUND

A variety of techniques are currently available for efficient amplification of nucleic acids even from a few starting nucleic acid templates resulting in a large number of amplified products. These include polymerase chain reaction (PCR), rolling circle amplification (RCA) and strand displacement amplification (SDA). Due to higher amplification efficiencies of these techniques, even the slightest contamination of the reagents/reagent solutions employed in such amplification reactions with an undesired nucleic acid molecule may result in a huge amount of false amplification products. If such an amplification were used for diagnostic applications, this would likely result in a false-positive diagnosis.

Reagents or reagent solutions that are used in nucleic acid amplification reactions may get contaminated in various ways. For example, contamination may arise from carry-over amplification product (amplicons) of previous amplification reactions, from the site from which the sample for amplification is collected, by exogenous DNA in the laboratory environment or from reagents or reagent solutions used for amplification reaction.

Various pre-amplification sterilization procedures have been developed to minimize amplicon carry-over. For example, deoxythymidine triphosphate (dTTP) is substituted for deoxyuridine triphosphate (dUTP) in PCR amplifications to make PCR products distinguishable from template DNA. Use of enzyme uracil-N-glycosylase (UNG) in a pre-amplification step cleaves the carry-over amplicons at the incorporated uracil residues. In amplification reactions using the same primers and the same target sequences, enzymatic removal of amplicons from previous similar amplification reactions has also been reported. These methods take advantage of the fact that the contaminant amplicon carries its primer sites at or near the ends of the molecule whereas virtually all other template DNA molecules not arising themselves from a previous PCR reaction, do not have their primer sites so located.

Single strand-specific exonuclease has been used for amplicon de-contamination during strand displacement amplification (SDA) reaction wherein either (or both) the target nucleic acid or the amplicons are in single stranded form. In such methods, even though both the target and amplicons are attacked, due to the short length of amplicons (25-2,000 nucleotides) and their lack of secondary structures, the amplicons are preferentially cleaved.

Use of selectively activable enzymes such as micrococcal nuclease and of DNA-binding agents have been employed to de-contaminate the reagent solution. Enzymatic, physical or chemical pre-treatment of the sample has also been employed to remove or inactivate a contaminating DNA that is originating from the site from where the sample is collected.

Apart from amplicon carry-over, reagents and reagent solutions commonly used to amplify nucleic acids may contain unwanted nucleic acid contaminants that could potentially interfere with standard nucleic acid amplification protocols and procedures. Contaminating DNA may be much longer than that of a primer or an amplicon and specific information about the contaminating DNA may often be minimal. During amplification reactions, false amplification products may also be formed by the inherent contamination of the reagents used for such reactions. For example, polymerization enzymes such as DNA polymerases that are used in amplification reactions may inherently carry contaminating nucleic acids. Standard protein purification techniques might not be sufficient enough to de-contaminate such nucleic acid-binding proteins effectively. So, there exists a need for specific treatments to de-contaminate the reagents and the reagent solutions used for amplification reactions.

FIELD OF INVENTION

The present invention relates generally to methods and kits for removing contaminating nucleic acids from reagents or reagent solutions used in nucleic acid amplification reactions. By de-contaminating the reagents or reagent solutions, the present methods help reduce the artifacts in DNA amplification reactions and improve the amplification efficiency.

BRIEF DESCRIPTION

One or more of the embodiments of the present invention are directed to methods for removing, digesting, degrading or otherwise inactivating nucleic acids (e.g., contaminating nucleic acids), which may be present in a reagent (e.g., a nucleic acid polymerase) or a reagent solution (e.g., a buffer solution used in a reaction mixture) used for nucleic acid amplification reactions. Generally, these nucleic acids are referred as contaminating nucleic acids, however, the methods of the present invention are generally applicable to all nucleic acids that are desired to be removed, digested, degraded or otherwise inactivated. According to the methods of the present invention, the nucleic acids are altered by digestion or degradation in a manner to prevent their further activity or reactivity in nucleic acid amplification reactions. The contaminating nucleic acids are either removed or inactivated to render them inert. One or more of the embodiments of the present invention help to increase the amplification efficiency of target nucleic acids (e.g., a target DNA). For example, during amplification reactions involving small amounts of target nucleic acids (e.g., single molecule DNA amplification), it is advisable to begin with reagents that are nucleic acid contamination-free to reduce false-positives.

In some embodiments, the present invention provides methods for processing a polymerase solution. The processing of the polymerase solution comprises steps for de-contaminating the polymerase solution. It may further comprise steps of using the processed polymerase solution for amplification reactions. In one embodiment, the method comprises the steps of contacting the polymerase solution comprising a proofreading DNA polymerase and a contaminating nucleic acid with a divalent cation and incubating the polymerase solution to allow the proofreading DNA polymerase to render the contaminating nucleic acid inert. In some embodiments, the methods for self-cleaning the polymerase solution utilize the intrinsic proofreading activity of the polymerase to degrade the contaminating nucleic acid. In some other embodiments, additional exonucleases are added to the polymerase solution to render the contaminating nucleic acid inert.

In some embodiments, the present invention provides methods to degrade a contaminating nucleic acid in a proofreading DNA polymerase. The method comprises the steps of contacting the proofreading DNA polymerase, comprising the contaminating nucleic acid, with a divalent cation to form a polymerase-cation mixture having a proofreading activity, and incubating the polymerase-cation mixture to allow the proofreading DNA polymerase to degrade the contaminating nucleic acid. In some embodiments, the contacting step and the incubating step are performed in the absence of any substantial amount of free nucleotides (dNTPs). In some specific embodiments, an exonuclease such as exonuclease I or exonuclease III or a combination of exonuclease I and exonuclease III may be added to the solution comprising proofreading DNA polymerase. In some embodiments, the method comprises de-contaminating a Phi29 DNA polymerase solution.

In some embodiments, the present invention provides methods for processing a primer solution comprising a nuclease-resistant primer. The method comprises the steps of contacting a primer solution with a nuclease and a divalent cation, wherein the primer solution comprises a contaminating nucleic acid; and incubating the primer solution to allow the nuclease to render the contaminating nucleic acid inert. The primer solution may further comprise free nucleotides and/or a single stranded DNA-binding protein. In some embodiments, one or more of exonuclease is used in the reaction, wherein one or more of the exonucleases is selected from the group consisting of exonuclease I, exonuclease III and combinations thereof.

In some embodiments, the present invention also provides methods to amplify a target nucleic acid. The method comprises the steps of (a) incubating a first solution with a first divalent cation to render a first contaminating nucleic acid inert, wherein the first solution comprises a proofreading DNA polymerase and the first contaminating nucleic acid (b) incubating a second solution with an exonuclease and a second divalent cation to render a second contaminating nucleic acid inert, wherein the second solution comprises a nuclease-resistant primer and the second contaminating nucleic acid (c) inactivating the exonuclease in the second solution (d) mixing the first solution and the second solution with a third solution comprising the target DNA and (d) amplifying the target DNA. The incubation of the first solution may be performed in the absence of free nucleotides (dNTPs). The first solution may further comprise an exonuclease and/or a single stranded DNA-binding protein (SSB protein). The second solution may further comprise free nucleotides (dNTPs). The target DNA may be amplified using other known methods such as, but not limited to, isothermal DNA amplification techniques such as rolling circle amplification (RCA) or multiple displacement amplification (MDA).

In some embodiments, the present invention provides a kit for DNA amplification. The kit may provide contamination-free reagents for DNA amplification or may provide components that could be used for making the reagents used in amplification reactions contamination-free. In one example embodiment, the kit comprises a proofreading DNA polymerase, a nuclease-resistant primer and an exonuclease. The kit may further comprise a single stranded DNA-binding protein and/or a buffer solution suitable for performing a reaction for degrading a contaminating DNA. In one example embodiment, the kit comprises a Phi29 DNA polymerase and a nuclease-resistant primer comprising at least one phosphorothioate nucleotide. In one specific example embodiment, the kit comprises an exonuclease chosen from exonuclease I, exonuclease III and combinations thereof.

DRAWINGS

These and other features, aspects and advantages of the present invention will become better understood when the following detailed description is read with reference to the accompanying figures.

Figure 5:
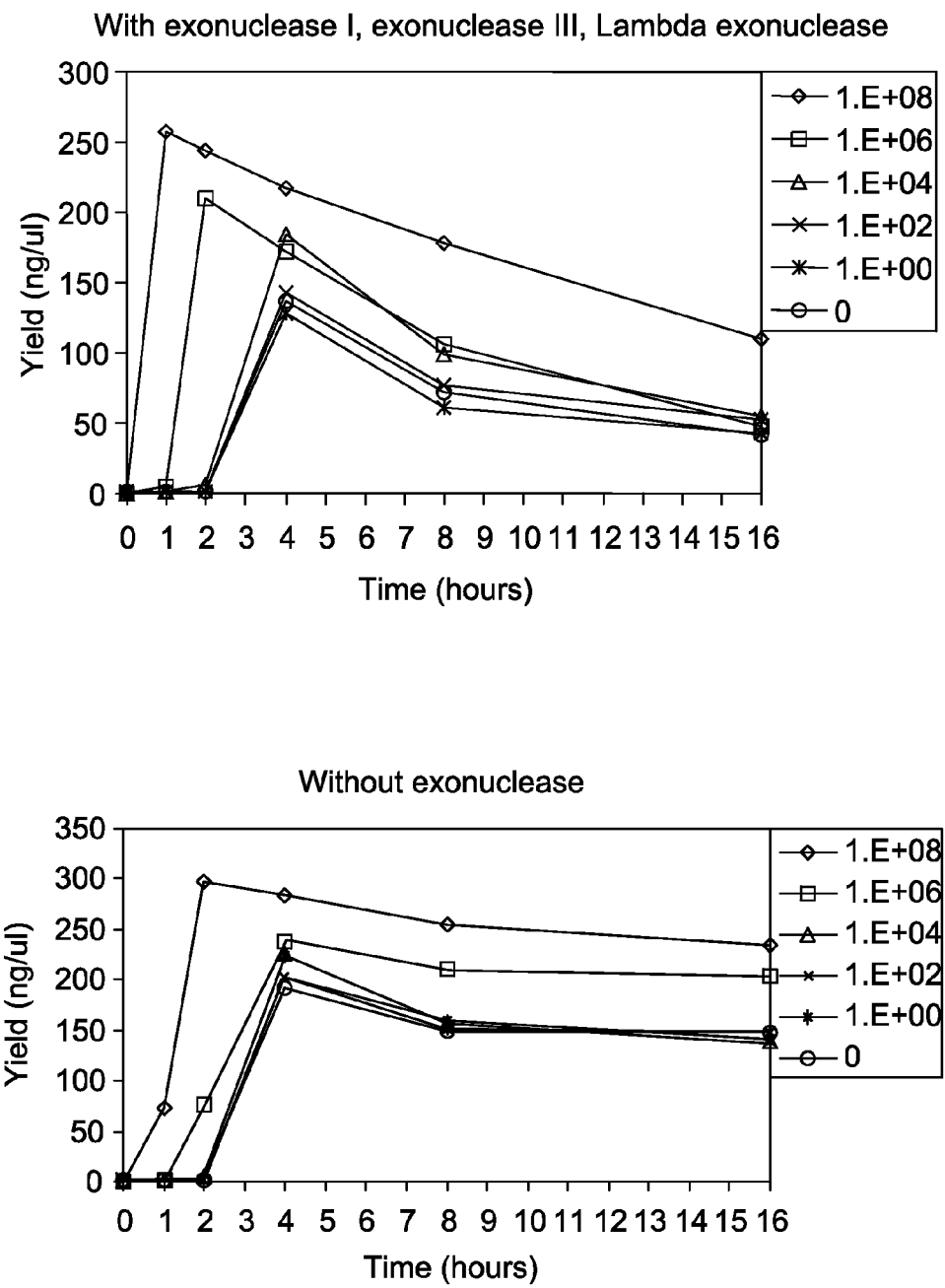
Figure 6:
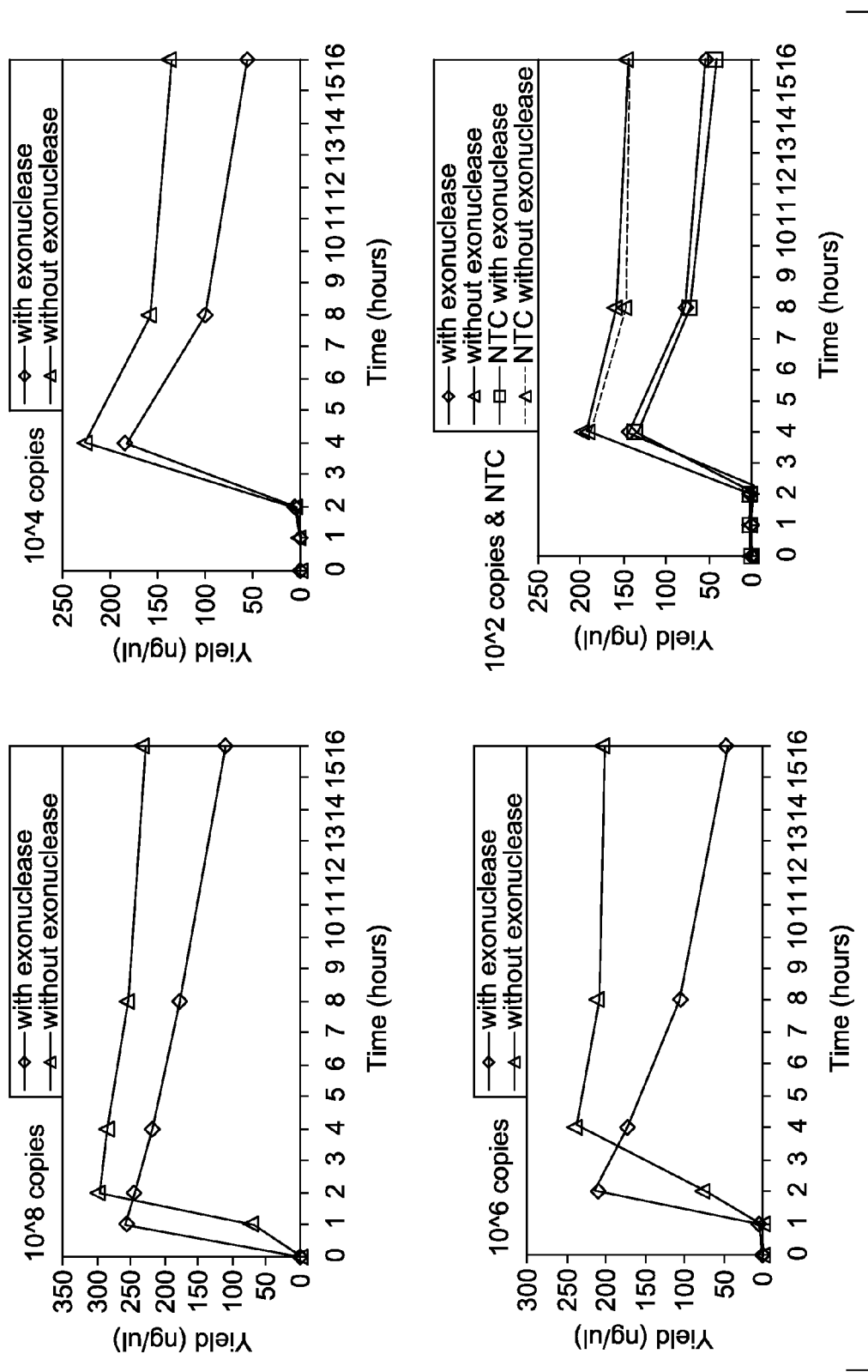

FIG. 5 illustrates the effect of an embodiment of the exonuclease treatment of a primer solution and a proofreading DNA polymerase solution on DNA amplification FIG. 6 illustrates the effect of an embodiment of the step of incubating the proofreading DNA polymerase with an exonuclease and magnesium ion on template DNA amplification. In this example embodiment, the exonucleases were not deactivated prior to template DNA amplification reaction.

Figure 7:
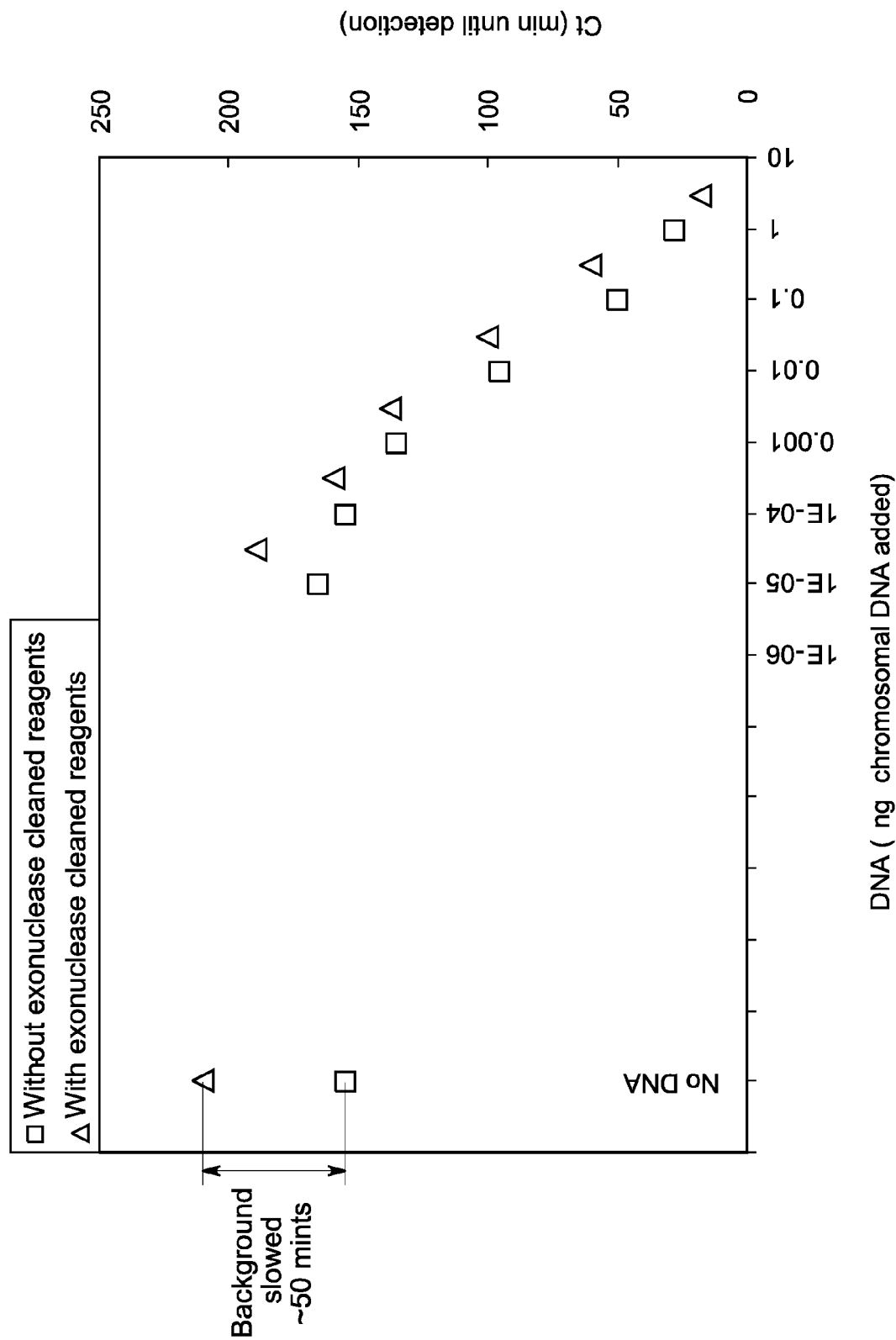

FIG. 7 illustrates the effect of an embodiment of the step of incubating Phi29 DNA polymerase and a primer solution with an exonuclease on a template DNA titration. In this example embodiment, pUC DNA is used as a template DNA and a nuclease-resistant hexamer sequence, NNNN*N*N is used as a primer. The template DNA is amplified using rolling circle amplification.

Figure 8:
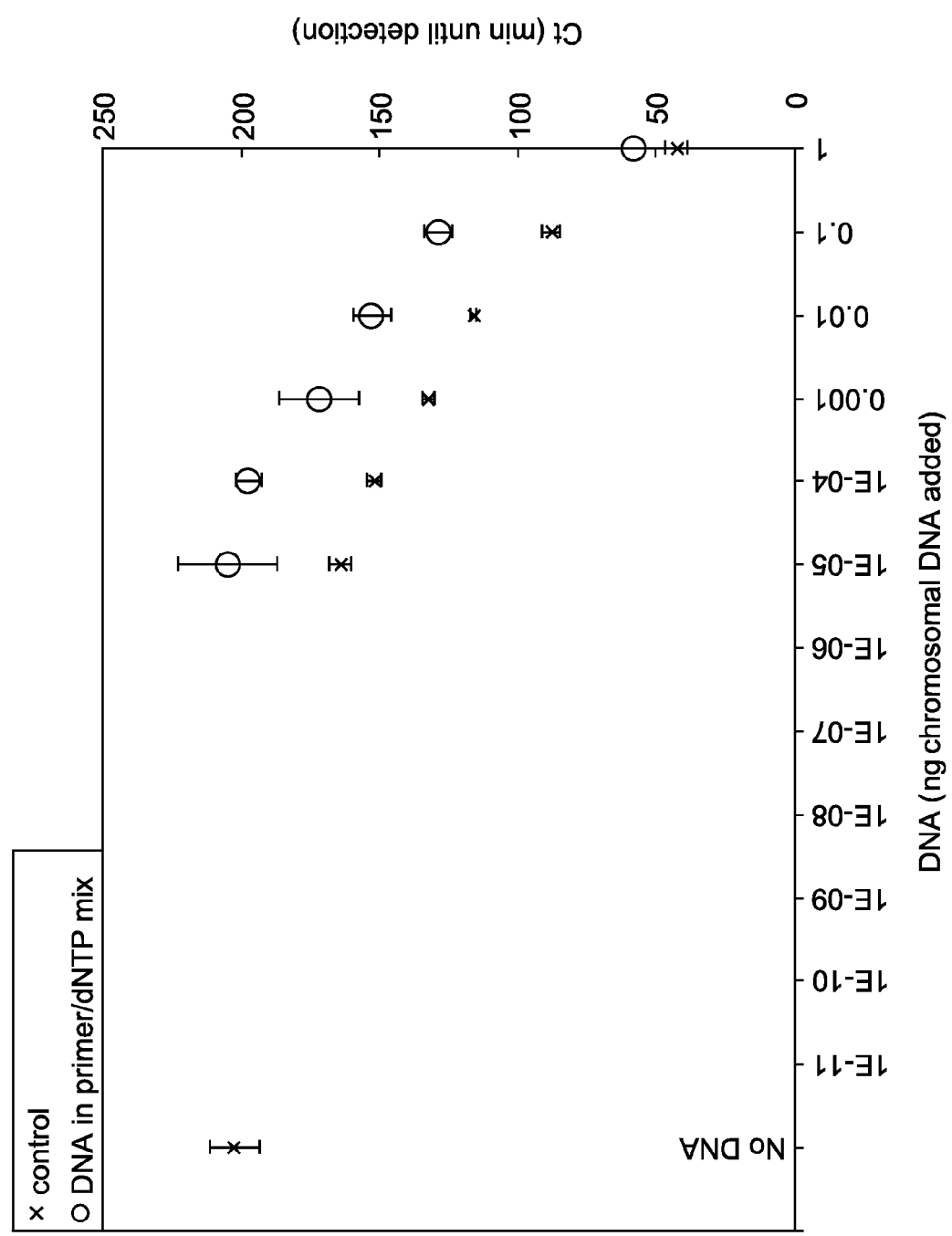
Figure 9:
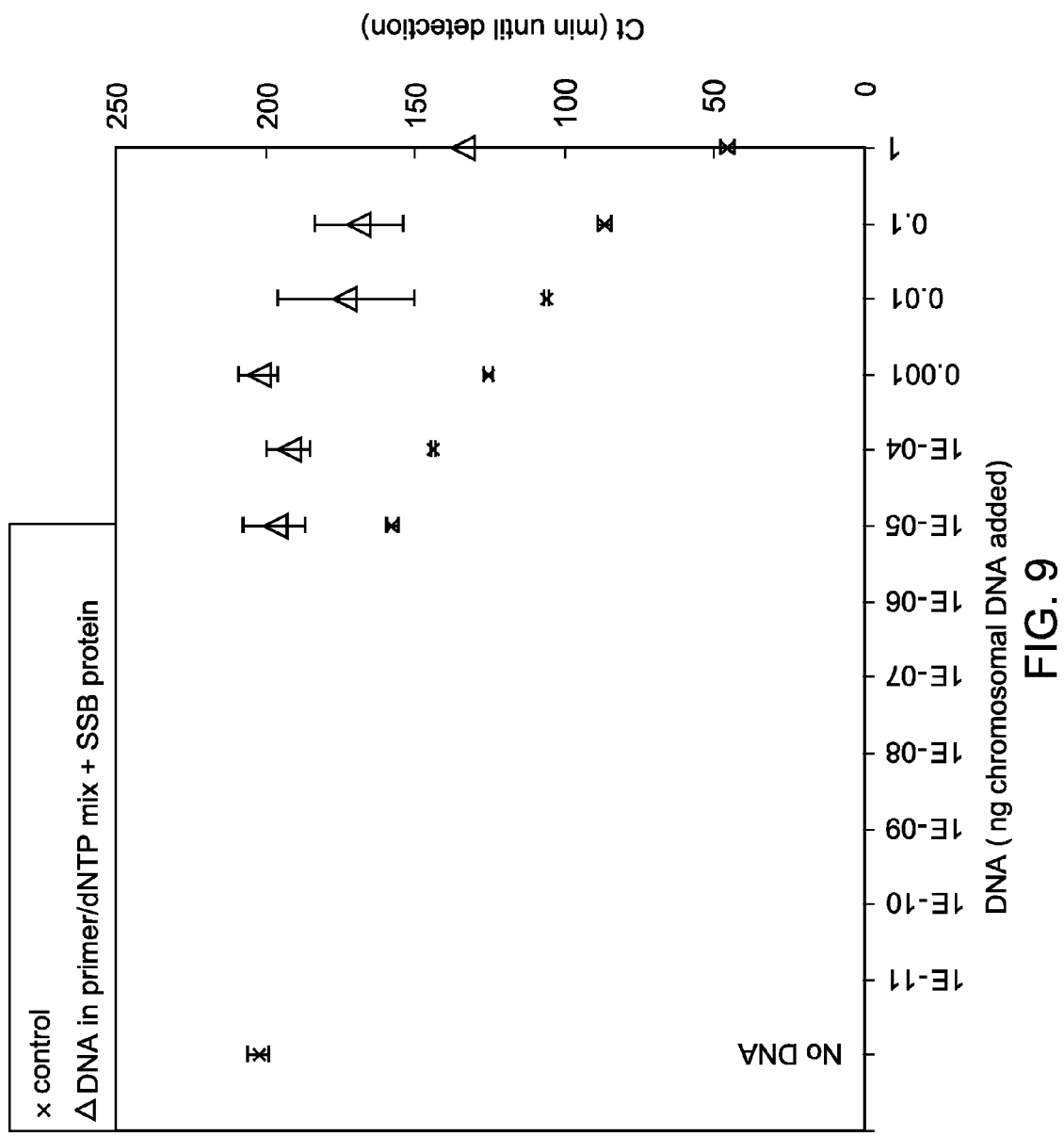
Figure 10:
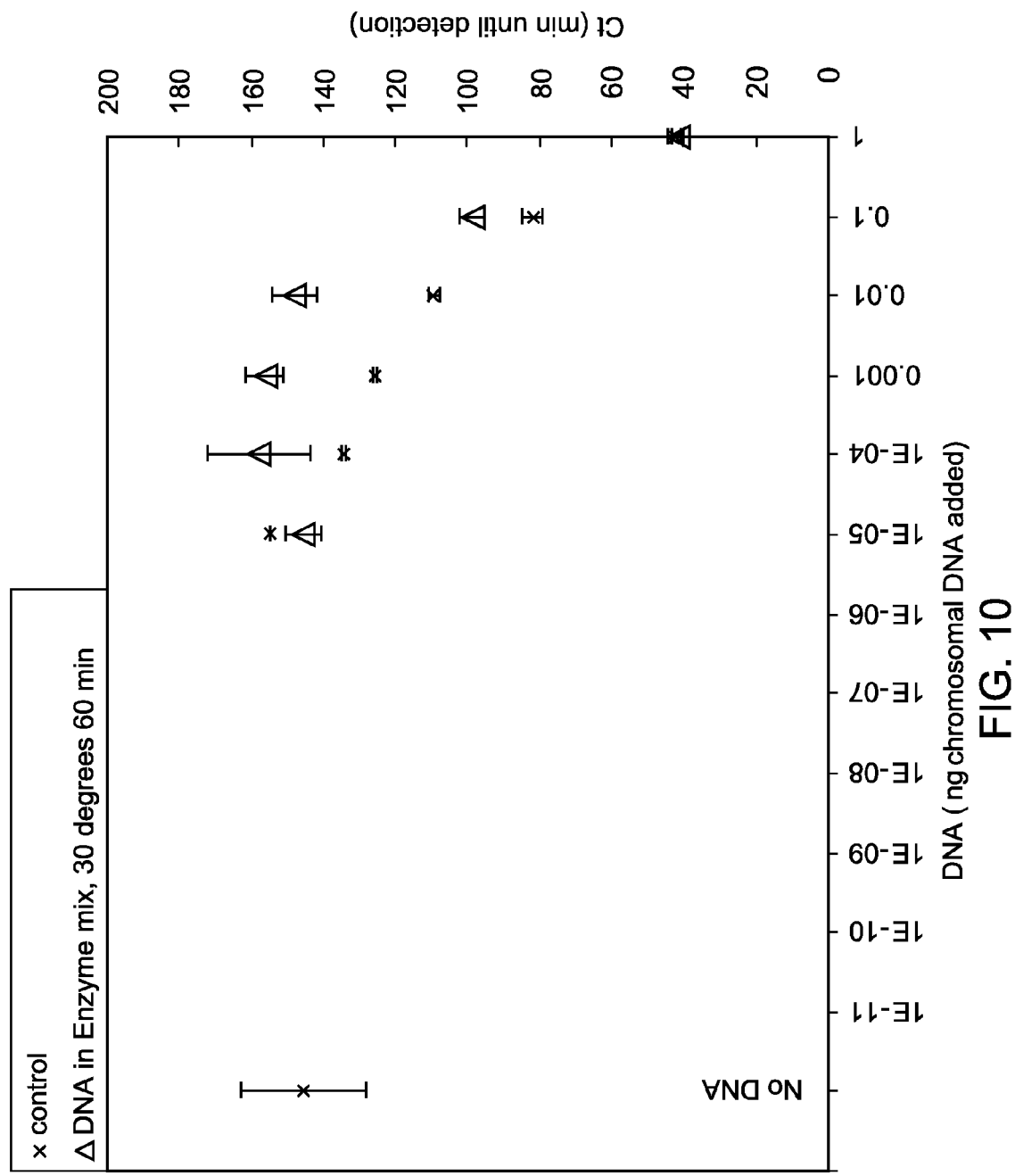
Figure 11:
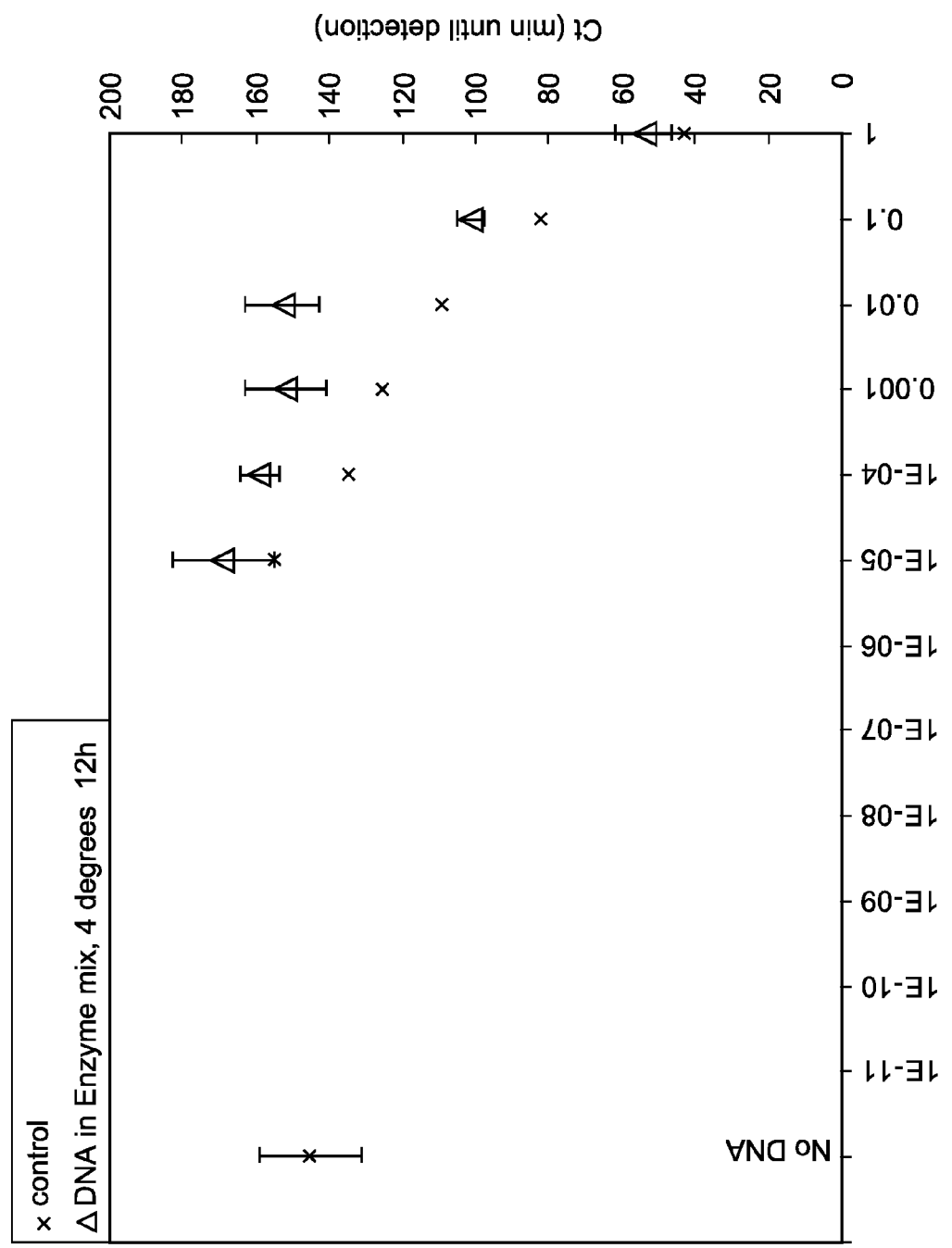

FIG. 8 illustrates the effect of an embodiment of the step of processing the reagents or reagent solutions with an exonuclease on a template DNA amplification FIG. 9 illustrates the effect of an embodiment of the step of processing the reagents or reagent solutions with an exonuclease and a single stranded DNA-binding protein (SSB protein) on a template DNA amplification FIG. 10 illustrates the effect of an embodiment of the step of processing the proofreading DNA polymerase solution with an exonuclease at 30° C. for 60 min. on a template DNA amplification FIG. 11 illustrates the effect of an embodiment of the step of processing the proofreading DNA polymerase solution with an exonuclease at 4° C. for 24 h. on a template DNA amplification

DETAILED DESCRIPTION

One or more embodiments of the present invention are directed at methods, reagents and kits useful for inactivating nucleic acids or otherwise rendering them inert in, for example, amplification reactions (e.g., DNA amplification reactions). Inactivation of nucleic acids (e.g., contaminating nucleic acids), may be desired in applications such as analytical, diagnostic, prognostic or forensic applications and the like. The precise use, including the choice of variables such as concentrations, volumes, incubation times, incubation temperatures, and the like will depend in large part on the particular application for which it is intended. It is to be understood that one of skill in the art will be able to identify suitable variables based on the present disclosure. For convenience, in this detailed description of various embodiments, the disclosed methods generally relate, but are not limited to, the removal of contaminating DNA in reagents and reagent solutions, such as those reagents and solutions for use in amplification reactions (e.g., PCR or isothermal DNA amplification methods). It will be within the ability of those skilled in the art, however, given the benefit of this disclosure, to select and optimize suitable conditions for using the methods in accordance with the principles of the present invention, suitable for these and other types of applications.

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified.

As used herein, the term "contaminating nucleic acid" refers to nucleic acid, which is present in a reagent, a reagent solution, or an apparatus, but is otherwise undesirable. That is, contaminating nucleic acid is any nucleic acid, which is not intended to be amplified, further characterized or present in an assay to be performed. In some embodiments, the contaminating nucleic acid is a deoxyribonucleic acid (DNA). For example, a DNA that is present in a reagent or reagent solution suitable for performing a DNA synthesis reaction, prior to adding a DNA template to be amplified, is considered to be a contaminating nucleic acid. The contaminating nucleic acid in a DNA synthesis reaction may act as a potential DNA template or a primer and thus participate in the DNA synthesis reaction, resulting in unwanted amplification products. So, it is desirable to remove such contaminating nucleic acid prior to addition of the DNA template to be amplified such that when the DNA template to be amplified is added to the solution, the contaminating nucleic acid will not interfere with the DNA synthesis reaction. Prior removal of contaminating DNA from the reagents and reagent solutions is generally desired to reduce artifacts during DNA synthesis reaction if the DNA template to be amplified is available only in limited amounts. In some embodiments, the contaminating nucleic acid is a ribonucleic acid (RNA).

As used herein, the term "render inert" refers to the altering or modifying of nucleic acid(s) such that the nucleic acid(s) cannot interfere with any subsequent chemical and/or biological reactions. The nucleic acid(s) can be rendered inert by chemical modification of the nucleic acid, for example, by removal of one or more functional groups such that the nucleic acid is unable to react with a DNA template or polymerase, for example. Nucleic acid may also be rendered inert by degrading or digesting the nucleic acid, for example, using an enzyme. Depending on the nature of the reagents (e.g., an enzyme), the mechanism by which the nucleic acid is rendered inert may vary. For example, in embodiments where the proofreading DNA polymerase is rendering the nucleic acid inert, the DNA may be rendered inert by the exonuclease activity of the proofreading DNA polymerase. In embodiments involving Phi29 DNA polymerase, the contaminating DNA may be rendered inert by the 3'→5' exonuclease activity of the Phi29 DNA polymerase. Here, the nucleic acid is rendered inert by digesting the nucleic acid to produce free nucleotides having a 3'-hydroxyl group and a 5'-phosphate group. Such nucleotides do not participate in subsequent DNA synthesis reaction.

As used herein, the term "render contaminating nucleic acid inert" refers to the process of modifying contaminated nucleic acids so that they cannot substantially interfere with subsequent chemical analysis and/or procedures, such as, but not limited to, isothermal DNA amplification or PCR. In some embodiments, this is achieved by degrading or digesting the contaminating nucleic acid. In some embodiments, rendering contaminating nucleic acid inert refers to a complete removal or a reduction in the amount of contaminating nucleic acid so that the contaminating nucleic acid does not interfere with the further biological/chemical reactions.

As used herein the terms "digesting" or "degrading" refer to breaking of bonds, for example, phosphodiester bonds, between two or more chemical groups. Preferably, digesting refers to breaking bonds between two or more nucleotides, such that the free nucleotides or nucleotide fragments are produced. In some embodiments, the digesting refers to breaking of bonds between two or more nucleotides such that the products are rendered inert. The digestion may lead to products, which can no longer react with the other components in the solution or participate in subsequent reactions, for example, in a DNA polymerization reaction. For example, digestion of contaminating nucleic acids may lead to nucleotides or nucleotide fragments, which cannot act as a primer or a template for a subsequent DNA synthesis reaction.

As used herein, the terms "reagent solution" or "solution suitable for performing a DNA synthesis reaction" refer to any or all solutions, which are typically used to perform an amplification reaction/DNA synthesis. It includes, but is not limited to, solutions used in isothermal DNA amplification methods and/or PCR. The solution suitable for DNA synthesis reaction may comprise buffer, salts, and nucleotides. It may also further comprise primers and a DNA template to be amplified.

As used herein, the term "incubating" refers to the process of keeping a solution or reaction mixture at a pre-determined temperature and pressure for a pre-determined period of time to achieve a specific reaction. The temperature and the period of incubation are suitably selected such that the purpose of the incubation (e.g., rendering contaminating nucleic acid inert) is achieved at the end of incubation. The incubation time and temperature may vary depending on the kinetic properties of the reagents/enzyme that are involved in the reaction. Depending on the nature and properties of the reagents/solutions involved, one skilled in the art, given the benefit of this disclosure, will be able to select suitable temperature and time period for incubation.

As used herein the term "reaction mixture" refers to the combination of reagents or reagent solutions, which are used to carry out one or more chemical analysis or biological assays. In some embodiments, the reaction mixture includes all necessary components to carry out a DNA synthesis/amplification reaction.

As used herein, the term "amplification" or the term amplifying refers to the production of multiple copies of a target nucleic acid sequence or the production of multiple nucleic acid sequence copies that are complementary to the target nucleic acid sequence.

As used herein, the term "nucleotide" refers to both natural and modified nucleoside phosphates. The term "nucleoside" refers to a compound having a purine, deazapurine, pyrimidine or a modified base linked at the 1' position or at an equivalent position to a sugar or a sugar substitute (e.g., a carbocyclic or an acyclic moiety). The nucleoside may contain a 2'-deoxy, 2'-hydroxyl or 2',3'-dideoxy forms of sugar or sugar substitute as well as other substituted forms. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but not limited to, a deoxyribonucleoside triphosphate (dNTP).

The term "free nucleotides", as used herein, refers to the nucleotides that are free in the solution or reaction mixture. The free nucleotides may or may not participate in a polymerization reaction (e.g., DNA synthesis reaction). The chances of participation or reactivity of the free nucleotides in a polymerization reaction depends on the chemical nature of the nucleotides that are freely available. For example, if the free nucleotide is dNTP, it is capable of participating in a polymerization reaction. The term "substantial amount of free nucleotides" refers to the minimum amount of nucleotides that is required to switch the primary activity of a proofreading DNA polymerase from its exonuclease activity/proofreading activity to its DNA synthesis activity.

The term "oligonucleotide", as used herein, refers to oligomers of nucleotides or derivatives thereof. Throughout the specification, whenever an oligonucleotide is represented by a sequence of letters, the nucleotides are in 5'→3' order from left to right. In the letter sequence, letter A denotes adenosine, C denotes cytosine, G denotes guanosine, T denotes thymidine, W denotes A or T and S denotes G or C. N represents a random nucleic acid base (for example, N may be any of A, C, G, U or T). +N represents a synthetic, locked random nucleotide and *N represents a phosphorothioate modified random nucleotide.

As used herein, the term "primer" refers to a short linear oligonucleotide that hybridizes to a target nucleic acid sequence (e.g., a DNA template to be amplified). Primers may be specific primers or random primers. The specific primers are designed to have a sequence, which is the reverse complement of a pre-determined region of the target nucleic acid to which it anneals. Both the upper and lower limits of the length of the primer are empirically determined. The lower limit on primer length is the minimum length that is required to form a stable duplex upon hybridization with the target nucleic acid. Very short primers (usually less than 3 nucleotides long) do not form thermodynamically stable duplexes with target nucleic acid under hybridization conditions. Upper limit is determined by the possibility of having a duplex formation in a region other than the pre-determined nucleic acid sequence in the target nucleic acid. Suitable primer lengths are in the range of about 3 to about 100 nucleotides long. Suitable primer lengths may be about 3 to about 40 nucleotides long or may be about 3 to about 25 nucleotides long. In some embodiments, suitable primers are 6 nucleotides-long hexamers.

As used herein the term "DNA polymerase" refers to any enzyme that catalyzes the production/synthesis of a new DNA. DNA polymerase uses an existing DNA or RNA as a template for DNA synthesis and catalyzes the polymerization of deoxyribonucleotides alongside the template strand, which they 'read'. The newly synthesized DNA strand is complementary to the template strand. DNA polymerase can add free nucleotides only to the 3-hydroxyl end of the newly forming strand. It synthesizes oligonucleotides via transfer of a nucleoside monophosphate from a nucleoside triphosphate (NTP) or deoxyribonucleoside triphosphate (dNTP) to the 3'-hydroxyl group of a growing oligonucleotide chain. This results in elongation of the new strand in a 5'→3' direction. DNA polymerase can only add a nucleotide onto a pre-existing 3'-OH group. So, to begin a DNA synthesis reaction, a DNA polymerase needs a primer at which it can add the first nucleotide. Suitable primers include RNA and DNA.

As used herein the term "proofreading DNA polymerase" refers to any DNA polymerase that is capable of correcting its errors while performing DNA synthesis. Proofreading DNA polymerase possesses a 3'→5' exonuclease activity apart from its polymerase activity and this exonuclease activity is referred here as proofreading activity. Proofreading activity of such polymerases correct mistakes in the newly synthesized DNA. During DNA synthesis, when an incorrect base pair is recognized, the proofreading DNA polymerase reverses its direction by one base pair of DNA. The 3'→5' exonuclease activity of the enzyme allows the incorrect base pair to be excised (proofreading activity). Following base excision, the polymerase re-inserts the correct base and DNA synthesis continues. When free dNTPs are present in the solution/reaction mixture suitable for DNA synthesis, the primary activity of the proofreading DNA polymerase is DNA synthesis. However, when dNTPs are not available for DNA synthesis reaction, the primary activity of the proofreading DNA polymerase is its 3'→5' exonuclease activity. So, when dNTPs are not available for DNA synthesis, the proofreading DNA polymerases, due to their exonuclease activity, are capable of digesting/degrading DNA. Proofreading DNA polymerases may be or may not be specific toward digestion of DNA single-strands. In some embodiments, proofreading DNA polymerase include any DNA polymerase that is capable of digesting/degrading nucleic acids in the absence of substantial amounts of dNTPs in the reaction mixture.

Some of the proofreading DNA polymerases require the presence of a divalent cation for their proofreading activity as well as for their polymerase activity. Suitable divalent cations that can switch on the proofreading activity of the proofreading polymerases include, but are not limited to, magnesium and manganese.

In accordance with one or more embodiments, a method for processing a polymerase solution is disclosed. Processing may involve steps for de-contamination of the polymerase as well as its subsequent optional use in further reactions, for example, nucleic acid amplification. In some embodiments, the processing of the polymerase solution is performed to render a contaminating nucleic acid inert.

Nucleic acid contamination of a polymerase may either be an inherent contamination or an extraneous contamination. Inherent contamination refers to the contamination of the polymerase by itself; i.e., the polymerase is intrinsically contaminated with a contaminating nucleic acid. Being a nucleic acid-binding enzyme, conventional methods of protein purification is often insufficient to devoid the polymerase with contaminating nucleic acids. Thus, the polymerase used for nucleic acid amplification may inherently be contaminated with a contaminating nucleic acid, for example a contaminant DNA. The nucleic acid thus inherently present in the polymerase could interfere with a subsequent biological/chemical reaction, such as a template DNA amplification. For example, such contaminating nucleic acids may act as a primer or as a template DNA during subsequent DNA amplification reaction. In embodiments where the contaminant DNA is present in the polymerase itself, the methods may comprise self-cleaning the polymerase by rendering the contaminating DNA inert. A solution comprising the polymerase may also be contaminated by extraneous means even though the polymerase by itself was devoid of any contaminating nucleic acids. For example, the polymerase solution may become contaminated by contaminants arising from lab environments, from the buffers/solutions used for making polymerase solution and the like. In such embodiments, the processing of the polymerase solution may comprise rendering the contaminating nucleic acid inert.

In some embodiments, the polymerase solution comprises a proofreading DNA polymerase. In such embodiments, the method for processing the polymerase solution comprises the steps of contacting the polymerase solution comprising a proofreading DNA polymerase and a contaminating nucleic acid with a divalent cation and incubating the polymerase solution to allow the proof-reading DNA polymerase to render the contaminating nucleic acid inert. In some embodiments, the contaminating nucleic acid may comprise a DNA.

In some embodiments, a method to degrade a contaminating nucleic acid in a proofreading DNA polymerase comprises the steps of contacting the proofreading DNA polymerase containing the contaminating nucleic acid with a divalent cation to form a polymerase-cation mixture having a proofreading activity and incubating the polymerase-cation mixture to allow the proofreading DNA polymerase to degrade the contaminating nucleic acid. In one example embodiment, the proofreading DNA polymerase comprises a contaminating DNA and the processing of the proofreading DNA polymerase solution is performed to render the contaminating DNA inert. Incubating with divalent cation activates the proofreading activity of the proofreading DNA polymerase and the nucleic acid is rendered inert by the intrinsic exonuclease activity of the proofreading DNA polymerase. In some embodiments, the exonuclease activity of the proofreading DNA polymerase may be specific to single stranded DNA. The contacting and the incubating steps are performed in the absence of any substantial amount of free nucleotides (dNTPs). In one embodiment, the contacting and the incubating steps are performed in the absence of dNTPs. When dNTPs are absent in the solution, the primary activity of the proofreading DNA polymerase in presence of the divalent cation is not the DNA synthesis but is its exonuclease activity/proof reading activity. The term "substantial amount of free nucleotides" refers to the minimum amount of nucleotides that is required to switch the primary activity of the proofreading DNA polymerase from the exonuclease activity/proofreading activity to the DNA synthesis activity. In some embodiments, the contaminating nucleic acid is digested or degraded to make them inert. The digestion or degradation may result in a complete removal of the contaminating nucleic acid or may result in a reduction of its amount to an extent that it does not interfere with subsequent steps, for example, a DNA amplification reaction.

In some embodiments, the proofreading DNA polymerase comprises a thermally stable DNA polymerase. Proofreading DNA polymerase may be a thermophilic DNA polymerase or a mesophilic DNA polymerase. Any proofreading DNA polymerase known in the art could be used in the present invention. Examples of proofreading polymerases that are suitable for use in the present invention include, but not limited to, Phi29 DNA polymerase, hi-fidelity fusion DNA polymerase (for e.g., *Pyrococcus*-like enzyme with a processivity-enhancing domain from New England Biolabs, MA), Pfu DNA polymerase from *Pyrococcus furiosus* (Strategene, Lajolla, Calif.), Klenow fragment from DNA polymerase I of *E. coli*, T7 DNA polymerase, T4 DNA polymerase, DNA polymerase from *Pyrococcus* species GB-D (New England Biolabs, MA) and DNA polymerase from *Thermococcus litoralis* (New England Biolabs, MA).

Any divalent cation that can activate the exonuclease/proofreading activity of a proofreading DNA polymerase may be used in the methods. Suitable divalent cations include, but are not limited to manganese and magnesium ions. Depending upon the proofreading polymerase and the divalent cation used, the concentration of the divalent cation that is required for the proofreading DNA polymerase to render the contaminating DNA may vary. Typically a molar excess of divalent cations are used with respect to the proofreading DNA polymerase. Under such conditions, majority of the proofreading DNA polymerases are proofreadingly active. One skilled in the art given the benefit of this disclosure will be able to select and optimize the concentration of the divalent cations.

In some embodiments, magnesium ions are used as a suitable divalent cation. Usually, the concentration of the magnesium ions may range from about 5 mM to about 50 mM. In some embodiments, the concentration of the magnesium ions ranges from about 10 mM to about 30 mM. In some embodiments, 20 mM magnesium ions are used.

Proofreading DNA polymerase solution is incubated with the divalent cation for a specified amount of time that is sufficient to render the contaminating nucleic acid inert. The incubation time typically varies with the kinetic properties of the proofreading DNA polymerase and the divalent cation that are being used. The incubation time may also depend on the temperature at which the incubation is performed. The incubation time that is required to render the contaminating nucleic acid inert may be optimized by analyzing the extent of de-contamination. The extent of de-contamination can be tested by various techniques known in the art for characterizing the presence of nucleic acids. For example, after the incubating step, a DNA polymerase synthesis reaction may be carried out without adding any target template DNA to determine if contaminant DNA is amplified (false-positive signal). Extent of the reduction of DNA contamination could be assessed either by the absence of false-positive signal (no contaminant DNA getting amplified) or by the extended kinetics of contaminant DNA amplification (slower rate of contaminant DNA amplification). Suitable incubation time may range from about 5 min to about 24 h. In some embodiments, the incubation time may range from about 1 min to 100 min.

The temperature at which the incubation is performed depends primarily on the nature of the proofreading DNA polymerase used. The maximum temperature that could be used in particular reaction is limited by the stability of the proofreading DNA polymerase and the minimum temperature that could be employed for the incubation is limited by the proofreading activity of the proofreading DNA polymerase at that temperature. For example, when a thermally stable DNA polymerase is used, the incubation may be performed at a temperature as high as 105° C. In some embodiments, the incubation temperature may range from about −20° C. to about 95° C. In some embodiments, the suitable incubation temperature ranges from about 4° C. to about 45° C. In some embodiments, the incubation is performed at a temperature between about 10° C. to about 35° C. In one embodiment, the incubation is performed at about 30° C. for about 1 h.

In some embodiments, a single stranded DNA-binding protein (SSB protein), which binds preferentially to single stranded DNA, is added to the solution comprising the proofreading DNA polymerase. The SSB protein may either be added to the polymerase solution prior to the addition of the divalent cation or it may be added to the polymerase-cation mixture. In some embodiments, the additions of SSB proteins assist the intrinsic exonuclease activity of the proofreading DNA polymerase. Suitable SSB proteins that could be used in the present invention include, but not limited to, extremely thermostable single stranded DNA-binding protein (ET SSB from New England Biolabs, MA), *E. coli* RecA, Tth RecA (RecA homolog isolated from *Thermus thermophilus* from New England Biolabs, MA), phage T4 gene-32 protein and *E. coli* SSB protein.

In some embodiments, an exonuclease is added to the solution comprising the proofreading DNA polymerase. The exonuclease may either be added to the polymerase solution prior to the addition of the divalent cation or it may be added to the polymerase-cation mixture. In some embodiments, the added exonuclease is a double strand-specific exonuclease. In some embodiments, the added exonuclease is a DNA double strand-specific exonuclease and it degrades a double-stranded DNA preferentially. The added exonuclease may either be a 5'→3' (i.e., degrades a DNA from the 5' end) or a 3'→5' exonuclease. In some embodiments, a combination of exonucleases is used. Non-limiting examples of suitable exonucleases that could be used in the present invention include exonuclease I, exonuclease III, exonuclease VII, exonuclease T, Mung Bean nuclease, Nuclease BAL-31, T7 gene 6 exonuclease, spleen exonuclease, T5 D15 exonuclease and lambda exonuclease.

In yet another embodiment, an endonuclease is added to the solution comprising the proofreading DNA polymerase. This is particularly useful in embodiments wherein the contaminating nucleic acid may include a circular DNA. Endonucleases act on circular DNA and nick them. Once the nick is made, the proofreading DNA polymerase or the exonuclease can act on the contaminant, nicked DNA and degrade them to make them inert. Nonlimiting examples of suitable endonucleases include DNAses such as DNAse I.

In some embodiments, the solution comprising the proofreading DNA polymerase may further comprise a non-proofreading DNA polymerase. Suitable examples of non-proofreading DNA polymerase that could be used include, but not limited to Taq DNA polymerase, large fragment of Bst DNA polymerase, exo (−) DNA Polymerase gene from *Pyrococcus* species GB-D (New England Biolabs, MA), exo (−) DNA Polymerase from *Thermococcus litoralis* (New England Biolabs, MA).

In some embodiments, the processing of the proofreading DNA polymerase solution include the steps of (a) contacting the proofreading DNA polymerase containing the contaminating nucleic acid with a divalent cation to form a polymerase-cation mixture having a proofreading activity (b) optionally adding at least one or more of exonuclease (c) optionally adding one or more of SSB protein (d) optionally adding one or more of endonuclease and (e) incubating the polymerase-cation mixture to degrade the contaminating nucleic acid. The addition of the divalent cation, the exonuclease, the SSB protein and the exonuclease to the solution comprising proofreading DNA polymerase and the contaminated nucleic acid may either be performed sequentially or simultaneously. In embodiments where the sequential addition is performed, the addition may be carried out in any particular order. For example, in some embodiments, the exonuclease and the divalent cation may be mixed first and then added to the proofreading DNA polymerase solution followed by the SSB protein. In some other embodiments, the proofreading DNA polymerase solution may be contacted with the SSB protein first and then the exonuclease and the divalent cation could be added. One skilled in the art, given the benefit of this disclosure, will be able to optimize these conditions.

In some embodiments, the proofreading DNA polymerase solution comprises a Phi29 DNA polymerase. In some embodiments, the Phi29 DNA polymerase solution containing a contaminated nucleic acid is incubated with a divalent cation at a specified temperature for a period of time that is sufficient to render the contaminating DNA inert. In some embodiments, the contaminating nucleic acid is a DNA. In some embodiments, magnesium ions are used as a suitable divalent cation. In some embodiments, the Phi29 DNA polymerase comprises a contaminating DNA; i.e., the contaminating DNA is inherently present with the Phi29 DNA polymerase. In some embodiments, the contaminating DNA is rendered inert by the intrinsic 3'→5' exonuclease activity of the Phi29 DNA polymerase upon incubation with magnesium ions. The contaminating DNA is digested to produce free nucleotides having a 3'-hydroxyl group and a 5'-phosphate group (e.g., deoxyribonucleoside-5'-monophosphate). In some embodiments, the Phi29 DNA polymerase is incubated with the divalent cation at a temperature that ranges between about −20° C. to about 42° C. In some embodiments, the Phi29 DNA polymerase is incubated with magnesium ions at a temperature ranging from about 4° C. to about 40° C. In some embodiments, the incubation is performed at a temperature between about 25° C. to about 35° C. In some embodiments, the incubation is performed at 30° C. The concentration of the magnesium ions required for the reaction depends on the concentration of the Phi29 DNA polymerase used. Typically, a molar excess of magnesium ions is used for the de-contamination reaction so that substantially all the Phi29 DNA polymerase is activated toward proofreading. In some embodiments, the range of magnesium concentration varies from about 5 mM to about 50 mM. Incubation period may ranges from about 1 min. to about 24 h. In some embodiments, the incubation period ranges from about 10 min. to 100 min. In some embodiments, the Phi29 DNA polymerase is incubated with magnesium ions at 4° C. for about 24 h. In some embodiments, the Phi29 DNA polymerase is incubated with magnesium ions at 37° C. for about 80 min. In some other embodiments, the Phi29 DNA polymerase is incubated with 20 mM magnesium ions at 30° C. for about 60 min.

The effectiveness of the removal of a contaminating DNA from a polymerase solution may depends on various factors such as (i) the specific proofreading DNA polymerase used (ii) the amount and/or length of the contaminating DNA (iii) the nature and/or amount of SSB protein used, if any (iv) the nature and/or amount of exonuclease used, if any (v) the reaction conditions (e.g., pH, salt and temperature) (vi) the amount and/or type of the divalent cation used and the like. One skilled in the art, given the benefit of this disclosure, will be able to empirically optimize the system by varying one or more of these variables and arrive at conditions that render the contaminating nucleic acid inert most efficiently.

The processing of the polymerase solution may further comprise the steps of using the processed polymerase solution for specific applications, for example, a nucleic acid polymerization reaction. In some embodiments, after the incubation with a divalent cation, once the contaminating nucleic acid is rendered inert, the incubated mixture can be directly used for a target DNA amplification reaction. In specific examples, a primer is added to the processed polymerase solution along with free nucleotides (dNTPs) and a DNA template. No removal of the divalent cation from the processed polymerase solution is necessary since the primary activity of the proofreading DNA polymerase automatically switches from proofreading to polymerization (DNA synthesis) once free dNTPs are present in the reaction mixture. In contrast, the presence of divalent cations may also be a necessary requirement for a subsequent reaction in some specific embodiments. Removal of degraded contaminating nucleic acids from the processed polymerase solution is also not needed since they have been rendered inert and cannot interfere with the subsequent DNA synthesis reaction. Even in the embodiments where an exonuclease is employed for processing the proofreading DNA polymerase solution, removal or inactivation of the exonuclease may not be required prior to a subsequent DNA amplification reaction if the concentration of the exonucleases is selected in such a way that they does not significantly interfere in the subsequent amplification reaction. So, no purification steps are necessary prior to the use of the processed polymerase solution in the subsequent DNA synthesis reaction. The methods provided herein to process a polymerase solution and/or its subsequent use in a DNA amplification reaction can either be manually performed or be automated. The embodiments of the present invention for removing contaminated nucleic acids, without the need to separate the digestion products prior to performing a DNA synthesis reaction, may be particularly useful for automating the entire process.

The DNA template to be amplified (target DNA template) may either be single-stranded or double-stranded. The DNA template can be a circular DNA, a linear DNA or a nicked DNA. The DNA template may be a genomic DNA or a cDNA. The free nucleotides used for the DNA template amplification may (dNTPs) include, but are not limited to, dATP, dGTP, dCTP and dTTP. Other components such as suitable buffers, salts and the like may also be added to the processed polymerase solution to allow the DNA amplification to occur efficiently. In embodiments, where an exonuclease is used in the processing of the polymerase solution, the deactivation of the exonuclease may or may not be required prior to the subsequent DNA template amplification.

The DNA template may be amplified using any of a variety of DNA amplification methods known in the art. For example, the amplification of the DNA template may be performed using thermal cycling methods or using isothermal DNA amplification methods. Non-limited examples for DNA amplification methods that could be used in the present invention include polymerase chain reaction (PCR), ligase chain reaction (LCR), self-sustained sequence replication (SSR), nucleic acid sequence-based amplification (NASBA) and amplification with Qβ-replicase. In some specific embodiments, a DNA template is amplified using rolling circle amplification (RCA) method. The RCA may either be a linear RCA (LRCA) or an exponential RCA (ERCA). In some embodiments, multiply-primed rolling circle amplification (MPRCA) is employed. In some other embodiments, a DNA template is amplified using strand displacement amplification reaction (SDA). In another embodiment, the DNA template is amplified using multiple displacement amplification (MDA).

The primers used in the amplification reaction typically depend on the sequence of the DNA template to be amplified and the selected amplification method. One skilled in the art, given the benefit of this disclosure, will be able to design and select suitable primers depending on the sequence and the nature of the DNA template to be amplified. Either a single primer or multiple primers could be used for amplification. The primer employed in the present disclosure may either be a specific primer or a random primer. Specific primers have or are engineered to have, a nucleotide sequence that is complementary, in the Watson-Crick sense, to a sequence present in the target DNA template. Random primers have nucleotide sequences unrelated to the nucleotide sequences of the DNA template resulting in hybridization of the primers with the DNA template at random locations. In some embodiments, the primer comprises a nuclease-resistant primer, for example, a primer resistant to an exonuclease. Exonuclease-resistant primers useful in the methods disclosed herein may include modified nucleotides to make them resistant to the exonuclease digestion. For example, a primer may possess one, two, three or four phosphorothioate linkages between nucleotides at the 3' end of the primer sequence. In some embodiments, the present invention relate to processes wherein the primers contain at least one nucleotide that makes the primer resistant to degradation, particularly by an exonuclease and more particularly by a 3'→5' exonuclease. The modified nucleotide may be a phosphorothioate nucleotide. The modified nucleotide is commonly a 3'-terminal nucleotide but the method of the present invention also relates to embodiments wherein such a nucleotide is located at a position other than the 3'-terminal position. When the modified nucleotide is located at positions other than the 3'-terminal end of a primer sequence, the 3'-terminal nucleotide of said primer may be removed by the 3'→5' exonuclease activity. In some embodiments, a random hexamer primer is used that is resistant to 3'→5' exonuclease activity. In some embodiments, primers comprising the sequences such as WWNN*N*S or NNNN*N*N is used as a suitable primer. In these cases, the primer sequences may have two phosphorothioate nucleotides at the 3'-terminal end (* represents a phosphorothioate bond between the nucleotides). In some specific embodiments, multiple primers are used for the DNA template amplification. In some embodiments, the multiple primers are selected from the group consisting of primers sensitive to exonuclease activity, primers resistant to exonuclease activity and a mixture of primers sensitive to exonuclease activity and resistant to exonuclease activity.

The present invention further provides embodiments of methods to process reagent solutions other than a polymerase solution (for e.g., nucleotide solution and primer solution) that are commonly used in DNA amplification reactions.

In some embodiments, the methods comprise processing a nucleotide solution comprising free nucleotides (dNTPs) and a contaminating nucleic acid. In some embodiments, the processing of the nucleotide solution is performed to render the contaminating nucleic acid inert (de-contamination of the nucleotide solution) to yield a processed nucleotide solution. The method comprises the steps of contacting the nucleotide solution with a nuclease and a divalent cation and incubating the nucleotide solution to allow the nuclease to render the contaminating nucleic acid inert. In some embodiments, the nucleotide solution may further comprise a nuclease-resistant primer. In some embodiments, the processing of the nucleotide solution further comprises steps describing the use of the processed nucleotide solutions in specific applications, for example, a DNA amplification reaction.

Any divalent cation that can activate the nuclease may be used in the processing of the nucleotide solution. Some non-limiting examples include magnesium and manganese. The concentration of the divalent cation primarily depends on the concentration of the nuclease. Some of the parameters that determine the concentration of the nuclease include the amount of contaminating nucleic acid, the turn-over of the particular nuclease used and other kinetic parameters for the nuclease activity. In some embodiments, a molar excess of the divalent cation with respect to the nuclease is used in the processing of the nucleotide solution.

The nucleotide solution is incubated with the nuclease and the divalent cation for a period of time that is sufficient to render the contaminating nucleic acid inert. The incubation time may vary with the kinetic properties of the nuclease and the divalent cation that is being used. The incubation time may also depend on the temperature at which the incubation is performed. Incubation time may be optimized by analyzing the efficiency of the de-contamination process. The efficiency can be tested by various techniques known in the art for characterizing the presence of nucleic acids. Suitable incubation time may range from about 5 min. to about 3 h. In some embodiments, the incubation time may ranges from about 1 min to about 100 min. In some embodiments, the nucleotide solution is incubated with the exonuclease and the divalent cation at 37° C. for about 60 min.

The temperature, at which the incubation of the nucleotide solution is performed, may vary by the nature of the particular nuclease used. The maximum temperature that may be used for the incubation is limited by the stability of the exonuclease and the minimum temperature that may be employed for the incubation is decided by the nuclease activity at that temperature. In some embodiments, the incubation is performed at a temperature at or below 50° C. In some embodiments, the suitable incubation temperature ranges from about 0° C. to about 45° C. In some specific embodiments, the incubation is performed at a temperature between about 10° C. to about 40° C.

In some embodiments, methods for processing the nucleotide solution may further comprise adding a single-stranded DNA binding-protein (SSB protein). Suitable SSB proteins that may be used in the present invention include, but not limited to, extreme thermostable single stranded DNA-binding protein (ET SSB from New England Biolabs, MA), *E. coli* RecA, Tth RecA (RecA homolog isolated from *Thermus thermophilus* from New England Biolabs, MA), phage T4 gene-32 protein and *E. coli* SSB protein. The addition of exonuclease, divalent cation and/or the SSB to the solution comprising free nucleotides and contaminated nucleic acid may either be performed sequentially or simultaneously. In embodiments where the sequential addition is performed, the addition may be carried out in any particular order. For example, in some embodiments, the exonuclease and the divalent cation may be mixed first and then added to the nucleotide solution followed by the SSB protein. In some other embodiments, the nucleotide solution may be contacted with the SSB protein first and then the exonuclease and the divalent cation could be added. In some embodiments, the nucleotide solution may further comprise a circular DNA template that is to be amplified.

A single exonuclease or a combination of exonucleases may be used to de-contaminate the nucleotide solution. Suitable exonucleases that may be used in the present invention include, but not limited, to exonuclease I, exonuclease III, exonuclease VII, T7 gene-6 exonuclease, spleen exonuclease, T5 D15 exonuclease, and lambda exonuclease. In one embodiment, a combination of exonuclease I and exonuclease III is used in the processing of the nucleotide solution.

The processing of a nucleotide solution may further comprise the steps of using such processed nucleotide solution for specific application, for example, a target DNA amplification. In some embodiments, after incubation of the nucleotide solution with a divalent cation and a nuclease, once the contaminating nucleic acid is rendered inert, the nuclease in the nucleotide solution may be inactivated prior to its use in a subsequent polymerization (e.g., DNA amplification) reaction. The nuclease may be inactivated by a variety of methods that is available in the art. In one example embodiment, the nuclease may be inactivated by thermal denaturation of the nuclease. The thermal denaturation of the nuclease may be achieved by incubating the processed nucleotide solution at a temperature at which the nuclease is not stable. The incubation is performed for a specified period of time that is sufficient to inactivate the nuclease. In some embodiments, this may be achieved by incubating the processed nucleotide solution at temperature at or above 65° C. In some embodiments, the processed nucleotide solution may be incubated at a temperature between 65° C. and about 95° C. The time that is sufficient to thermally inactivate the nuclease may vary depending on the temperature used and the type of nuclease involved. Typically, the thermal inactivation is performed for a time span of about 30 sec. to about 2 h. In some embodiments, the processed nucleotide solution may be incubated at about 85° C. for 15 min and then at about 95° C. for 5 min. One skilled in the art, given the benefit of this disclosure, will be able to optimize the time span and the temperature required for thermally inactivating the nuclease.

In some embodiments, methods for processing a primer solution comprising a nuclease-resistant primer contaminated and a contaminating nucleic acid are described. In some embodiments, the processing of the primer solution is performed to render the contaminating nucleic acid inert (de-contamination of the primer solution) to yield a processed primer solution. The method comprises the steps of contacting the primer solution with a nuclease and a divalent cation and incubating the primer solution to allow the nuclease to render the contaminating nucleic acid inert. The primer solution may further comprise free nucleotides (dNTPs). In some embodiments, the processing of the primer solution further comprises steps describing the use of the processed primer solutions in specific applications, for example, a DNA amplification reaction.

Any divalent cation that can activate the nuclease could be used in the processing of the primer solution. Some non-limiting examples include magnesium and manganese. The concentration of the divalent cation primarily depends on the concentration of the nuclease. Some of the parameters that determine the concentration of the nuclease include the amount of contaminating nucleic acid, the turn-over of the particular nuclease and other kinetic parameters for the nuclease activity. In some embodiments, a molar excess of the divalent cation with respect to the nuclease is used in the processing of the primer solution.

The primer solution is incubated with the nuclease and the divalent cation for a period of time that is sufficient to render the contaminating nucleic acid inert. The incubation time may vary with the kinetic properties of the nuclease and the divalent cation that is being used. The incubation time may also depend on the temperature at which the incubation is performed. Incubation time may be optimized by analyzing the efficiency of the de-contamination process. The efficiency may be tested by various techniques known in the art for characterizing the presence of nucleic acids. Suitable incubation time may range from about 5 min. to about 3 h. In some embodiments, the incubation time may ranges from about 1 min to about 100 min. In some specific embodiments, the primer solution may be incubated with the exonuclease and the divalent cation at 37° C. for about 60 min.

The temperature at which the incubation of the primer solution is performed may vary by the nature of the particular nuclease used. The maximum temperature that may be used for the incubation is limited by the stability of the exonuclease and the minimum temperature that may be employed for the incubation is decided by the nuclease activity at that temperature. In some embodiments, the incubation is performed at a temperature at or below 50° C. In some embodiments, the suitable incubation temperature ranges from about 0° C. to about 45° C. In some specific embodiments, the incubation may be performed at a temperature between about 10° C. to about 40° C.

In some embodiments, methods for processing the primer solution may further comprise adding a single-stranded DNA binding-protein (SSB protein). Suitable SSB proteins that may be used in the present invention include, but not limited to, extreme thermostable single stranded DNA-binding protein (ET SSB from New England Biolabs, MA), *E. coli* RecA, Tth RecA (RecA homolog isolated from *Thermus thermophilus* from New England Biolabs, MA) phage T4 gene-32 protein and *E. coli* SSB protein. The addition of exonuclease, divalent cation and/or the SSB to the solution comprising nuclease-resistant primer and contaminated nucleic acid may either be performed sequentially or simultaneously. In embodiments where the sequential addition is performed, the addition may be carried out in any particular order. For example, in some embodiments, the exonuclease and the divalent cation may be mixed first and then added to the primer solution followed by the SSB protein. In some other embodiments, the primer solution may be contacted with the SSB protein first and then the exonuclease and the divalent cation could be added. In some embodiments, the primer solution may further comprise a circular DNA template that is to be amplified.

In some embodiments, the primer is an exonuclease-resistant primer and the nuclease used in processing the primer solution is an exonuclease. In some preferred embodiments, the primer is resistant to 3'→5' exonuclease activity. Exonuclease-resistant primers useful in the methods disclosed herein may include modified nucleotides to make them resistant to exonuclease digestion. For example, a primer may possess one, two, three or four phosphorothioate linkages between nucleotides at the 3' end of the primer. In some embodiments, the present invention relate to processes wherein the primers contain at least one nucleotide that makes the primer resistant to degradation, particularly by an exonuclease and more particularly by a 3'→5' exonuclease. The at least one modified nucleotide may be a phosphorothioate nucleotide. Other nucleotide modifications known in the art that make a nucleotide sequence resistant to an exonuclease may be used as well. Modified nucleotide may be commonly located at 3'-terminal end of the primer sequence but the method of the present invention also relates to embodiments wherein such a nucleotide is located at positions other than the 3'-terminal position. When the modified nucleotides are present in positions other than the 3'-terminal position of a primer sequence, the 3'-terminal nucleotide of said primer may be removed by 3'→5' exonuclease. The primers employed in the present invention may either be a specific primer or a random primer. In some example embodiments, the primer comprises a random hexamer primer.

A single exonuclease or a combination of exonucleases may be used to de-contaminate the primer solution. Suitable exonucleases that may be used in the present invention include, but not limited, to exonuclease I, exonuclease III, exonuclease VII, T7 gene-6 exonuclease, spleen exonuclease, T5 D15 exonuclease and lambda exonuclease. In one embodiment, a combination of exonuclease I and exonuclease III is used in the processing of the primer solution.

The processing of a primer solution may further comprise the steps of using such processed primer solution for specific application, for example, a target DNA amplification. In some embodiments, after incubation of the primer solution with a divalent cation and a nuclease, once the contaminating nucleic acid is rendered inert, the nuclease in the primer solution may be inactivated prior to its use in a subsequent polymerization (e.g., DNA amplification) reaction. The nuclease may be inactivated by a variety of methods that is available in the art. In one specific embodiment, the nuclease may be inactivated by thermal denaturation of the nuclease. The thermal denaturation of the nuclease may be achieved by incubating the processed primer solution at a temperature at which the nuclease is not stable. The incubation is performed for a specified period of time that is sufficient to inactivate the nuclease. In some embodiments, this may be achieved by incubating the processed primer solution at temperature at or above 65° C. In some embodiments, the processed primer solution may be incubated at a temperature between 65° C. and about 95° C. The time that is sufficient to thermally inactivate the nuclease may vary depending on the temperature used and the type of nuclease involved. Typically, the thermal inactivation may be performed for a time span of about 30 sec. to about 2 h. In some embodiments, the processed primer solution may be incubated at about 85° C. for 15 min and then at about 95° C. for 5 min. One skilled in the art, given the benefit of this disclosure, will be able to optimize the time span and the temperature required for thermally inactivating the nuclease.

In accordance with certain embodiments, once substantially all the contaminating nucleic acid has been rendered inert, a DNA template to be amplified, a DNA polymerase and free nucleotides if not already present may be added to the processed primer solution to amplify the DNA template. Removal of degraded contaminating nucleic acids from the processed primer solution may not be required since they have been rendered inert and cannot interfere with the DNA synthesis reaction. The DNA polymerase that could be employed for amplifying the DNA template may be a proofreading DNA polymerase or a non-proofreading DNA polymerase. In some specific embodiments, a combination of a proofreading DNA polymerase and a non-proofreading DNA polymerase may be used for efficient amplification of the DNA template. The DNA template to be amplified may either be a single-stranded DNA template or a double-stranded DNA template. The DNA template may either be a circular DNA template, a linear DNA template or a nicked DNA template. The DNA template may be a genomic DNA template or a cDNA template. The DNA template may be amplified using any of a variety of DNA amplification methods known in the art. The amplification of the DNA template may be performed by using thermal cycling methods or by using isothermal DNA amplification methods. Non-limiting examples of DNA amplification methods that may be used in the present invention include polymerase chain reaction (PCR), ligase chain reaction (LCR), self-sustained sequence replication (SSR), nucleic acid sequence-based amplification (NASBA) and amplification using Qβ-replicase. In some specific embodiments, the DNA template is amplified using rolling circle amplification (RCA). The RCA may either be a linear RCA (LRCA) or an exponential RCA (ERCA). In some embodiments, multiply-primed rolling circle amplification (MPRCA) may be employed for amplifying the DNA template. In some other embodiments, the DNA template may be amplified using a strand displacement amplification reaction (SDA). In yet another embodiment, the DNA template may be amplified using a multiple displacement amplification (MDA).

In one embodiment, the DNA polymerase that is added to the processed primer solution comprises a proofreading DNA polymerase. In some specific embodiments, the solution of the proofreading DNA polymerase may also be processed to render any contaminating DNA inert prior to its addition to the processed primer solution. The polymerase solution may be processed by any of the methods that are described in the present disclosure for processing a polymerase solution. In one embodiment, a Phi29 DNA polymerase is used as a proofreading DNA polymerase. In one embodiment, the Phi29 DNA polymerase solution is processed by incubating the Phi29 DNA polymerase with magnesium ions at a specified temperature for a sufficient period of time to render the contaminating nucleic acid inert prior to its addition to the processed primer solution to carry out the template DNA amplification.

In some embodiments, the free nucleotides that are added to the processed primer solution may also be processed to render any contaminating DNA inert. The nucleotide solution may be processed by any of the methods that are described in the present disclosure for processing a nucleotide solution prior to its use in DNA amplification reaction. In one embodiment, the nucleotide solution may be processed by incubating the nucleotide solution with an exonuclease and magnesium ions at a specified temperature for a sufficient period of time to render the contaminating nucleic acid inert.

In some embodiments, the present invention provides methods for amplifying a target template DNA. The method uses reagents and reagent solutions that are substantially free of any contaminating nucleic acids. In some embodiments, the reagents and reagent solutions are processed by using the methods described in the present invention prior to their use in amplification reactions to amplify the template DNA. In some embodiments, a proofreading DNA polymerase solution may be processed to render the contaminating nucleic acid inert. In some other embodiments, a primer solution may be processed to render the contaminating nucleic acid inert. In some other embodiments, a nucleotide solution may be processed to render the contaminating nucleic acid inert. In some specific embodiments, the proofreading DNA polymerase solution, the nucleotide solution and the primer solution that are to be used in DNA amplification reaction are all processed to render the contaminating nucleic acid inert.

In a specific embodiment, a method to amplify a target DNA comprises the steps of (a) incubating a first solution with a first divalent cation to render a first contaminating nucleic acid inert, wherein the first solution comprises a proofreading DNA polymerase and the first contaminating nucleic acid, (b) incubating a second solution with an exonuclease and a second divalent cation to render a second contaminating nucleic acid inert, wherein the second solution comprises a nuclease resistant primer and the second contaminating nucleic acid, (c) inactivating the exonuclease in the second solution, (d) mixing the first solution and the second solution with a third solution comprising the target DNA and (e) amplifying the target DNA. The first divalent cation and the second divalent cation may or may not be the same. Similarly, the first contaminating nucleic acid and the second contaminating nucleic acid may or may not be the same. In one embodiment, the contaminating nucleic acid comprises a DNA.

In some embodiments, the incubation of first solution may be performed in the absence of any free nucleotides. The first solution may further comprise an exonuclease and/or a single strand-binding protein. In one embodiment the first solution comprises a Phi29 DNA polymerase. In yet another embodiment, the first solution comprises a mixture of proofreading DNA polymerase and a non-proofreading DNA polymerase. In a specific embodiment, the first solution comprises a combination of a Phi29 DNA polymerase and a Taq DNA polymerase. In some embodiments wherein the first solution comprises a Phi29 DNA polymerase, the first solution is incubated with magnesium ions at a specified temperature for a period of time that is sufficient to render the contaminating DNA inert. Here, the contaminating DNA may be rendered inert by the intrinsic 3'→5' exonuclease activity of the Phi29 DNA polymerase upon incubation with magnesium ions. The contaminating nucleic acid may be digested to produce free nucleotides having a 3'-hydroxyl group and a 5'-phosphate group (e.g., deoxyribonucleoside-5'-monophosphate). In some embodiments, the first solution comprising a Phi29 DNA polymerase may be incubated with the divalent cation at a temperature range between about −20° C. to about 42° C. In some embodiments, the first solution comprising the Phi29 DNA polymerase may be incubated with magnesium ions at a temperature ranging from about 10° C. to about 30° C. In some embodiments the incubation is performed at 25° C. The concentration of the magnesium required for the reaction may depend on the concentration of the Phi29 DNA polymerase used. Typically, a molar excess of magnesium ions are used for the de-contamination reaction so that substantially all the Phi29 DNA polymerase is activated toward proofreading by the magnesium ions. In some embodiments, the range of magnesium concentration varies from about 5 mM to about 50 mM and the incubation period may range from about 1 min. to about 24 h. In some embodiments, the incubation period ranges from about 10 min. to 100 min. In some embodiments, the first solution comprising the Phi29 DNA polymerase is incubated with magnesium ions at 30° C. for about 60 min.

In some embodiments, the second solution may further comprise free nucleotides. In some embodiments, the second solution may further comprise a circular DNA template. In one embodiment, the second solution comprises an exonuclease-resistant primer. In some embodiments, the second solution comprising the exonuclease-resistant primer may be incubated with the divalent cation in presence of one or more of exonucleases. In some embodiments, the second solution may be incubated with a combination of a single strand-specific exonuclease and a double strand-specific exonuclease. In some preferred embodiments, the second solution may be incubated with a mixture of exonuclease I and exonuclease III. Suitable exonucleases that may be used include, but not limited, to exonuclease I, exonuclease III, exonuclease VII, T7 gene-6 exonuclease, spleen exonuclease, T5 D15 exonuclease and lambda exonuclease. In some embodiments, magnesium ions are used as a suitable divalent cation.

In some embodiments, the second solution further comprises a single stranded DNA-binding protein (SSB protein). Suitable SSB proteins that may be used in the present invention include, but not limited to, extreme thermostable single stranded DNA-binding protein (ET SSB from New England Biolabs, MA), E. coli RecA, Tth RecA (RecA homolog isolated from Thermus thermophilus from New England Biolabs, MA) phage T4 gene-32 protein and E. coli SSB protein.

The exonuclease in the second solution may be inactivated by a variety of methods that is available in the art. In one specific embodiment, the exonuclease may be inactivated by thermal denaturation of the exonuclease. The thermal denaturation of the exonuclease may be achieved by incubating the second solution at a temperature at which the exonuclease is not stable. The incubation may be performed for a specified period of time that is sufficient to inactivate the exonuclease. In some embodiments, this may be achieved by incubating the second solution at temperature at or above 65° C. In some embodiments, the second solution may be incubated at a temperature between 65° C. and about 95° C. The time that is sufficient to thermally inactivate the exonuclease may vary depending on the temperature used and the type of exonuclease involved. Typically, the thermal inactivation is performed for a time span of about 30 sec. to about 2 h. In some embodiments, the second solution may be incubated at about 80° C. for 15 min and then at about 95° C. for 5 min. One skilled in the art, given the benefit of this disclosure, will be able to optimize the time span and the temperature required for thermally inactivating the exonuclease.

The target DNA in the third solution may either be a single-stranded or a double-stranded DNA. The target DNA may be in a circular form, a linear form or a nicked form. The target DNA may be a genomic DNA or a cDNA. In some embodiments, the target DNA may be obtained or derived from trace sources, such as single human cells, forensic samples, single bacterial cells, especially difficult to culture cells and single DNA molecule sources.

The target DNA in the third solution may be amplified using any of a variety of DNA amplification methods known in the art. The amplification of the target DNA may be performed by using thermal cycling methods or by using isothermal DNA amplification methods. Non-limiting examples of DNA amplification methods that may be used to amplify the target DNA include polymerase chain reaction (PCR), ligase chain reaction (LCR), self-sustained sequence replication (SSR), nucleic acid sequence-based amplification (NASBA) and amplification using Qβ-replicase. In some specific embodiments, the target DNA may be amplified using rolling circle amplification (RCA) method. The RCA may either be a linear RCA (LRCA) or an exponential RCA (ERCA). In some embodiments, multiply-primed rolling circle amplification (MPRCA) may be employed for amplifying the target DNA. In some other embodiments, the target DNA may be amplified using a strand displacement amplification reaction (SDA). In yet another embodiment, the target DNA may be amplified using a multiple displacement amplification (MDA).

Also provided herein are kits containing reagents required to practice the presently described inventive methods that permit de-contamination of a polymerase solution and a primer solution and their subsequent use in DNA amplification reactions. In some embodiments, the kit comprises a proofreading DNA polymerase, a nuclease resistant primer and an exonuclease. The kit may be used to process a polymerase solution or a nuclease resistant primer solution to render the contaminating nucleic acids inert. In some embodiments, the kit comprises a Phi29 DNA polymerase, a primer that is resistant to an exonuclease and the exonuclease. In some embodiments, the kit may further comprise reagents or reagent solution required for performing a DNA synthesis reaction.

Exonuclease-resistant primers in the kit may include modified nucleotides to make them resistant to exonuclease digestion. For example, the exonuclease-resistant primer may possess one or more of phosphorothioate linkages between the nucleotides. In some embodiments, the kit includes primers that contain at least one modified nucleotide that makes the primer resistant to exonuclease digestion. Modified nucleotide may be commonly located at 3'-terminal end of the primer sequence but it may also be located at positions other than the 3'-terminal position. The exonuclease-resistant primer included in the kit may either be a specific primer or a random primer. In some specific embodiments, the primer comprises a random hexamer primer. In some embodiments, the kit includes multiple exonuclease-resistant primers.

The kit may further comprise a single stranded DNA-binding protein (SSB protein). Suitable SSB proteins that may be included in the kit include, but not limited to, extreme thermostable single stranded DNA-binding protein (ET SSB from New England Biolabs, MA), *E. coli* RecA, Tth RecA (RecA homolog isolated from *Thermus thermophilus* from New England Biolabs, MA) phage T4 gene-32 protein and *E. coli* SSB protein.

In some embodiments, the kit further comprises at least one buffer that is suitable for performing a reaction for degrading contaminating DNA. The buffer comprises divalent cations. In some specific embodiments, the kit comprises at least one buffer comprising magnesium ions. Kit may comprise the pre-made buffer comprising the magnesium ions or it may comprise the necessary reagents required to produce the said buffer. In some specific embodiment, kit may comprise a salt of magnesium, for example, but not limited to, magnesium chloride ($MgCl_2$).

Suitable exonucleases that the kit may include are, for example, but not limited to, exonuclease I, exonuclease III, exonuclease VII, T7 gene-6 exonuclease, spleen exonuclease, T5 D15 exonuclease and lambda exonuclease. In some embodiments, the kit comprises exonuclease III. In some other embodiments, the kit may comprise a mixture of exonuclease I and exonuclease III. The combination of exonucleases may be provided in a single vessel or in multiple vessels. The kit provided herein may further include an instruction manual detailing the specific components included in the kit and the protocols for using them in a de-contamination reaction or in a DNA amplification reaction or both.

While only certain features of the invention have been illustrated and described herein, one skilled in the art, given the benefit of this disclosure, will be able to make modifications/changes to optimize the parameters. It is therefore, to be understood that the appended claims are intended to cover all such modifications and changes as fall within the true spirit of the invention. The examples are provided for illustrative purposes only, and should not be construed as limiting the scope of the present invention as defined by the appended claims. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "μmol": picomoles; "μL": microliters; "min.": minutes and "h.": hours.

Figure 1:
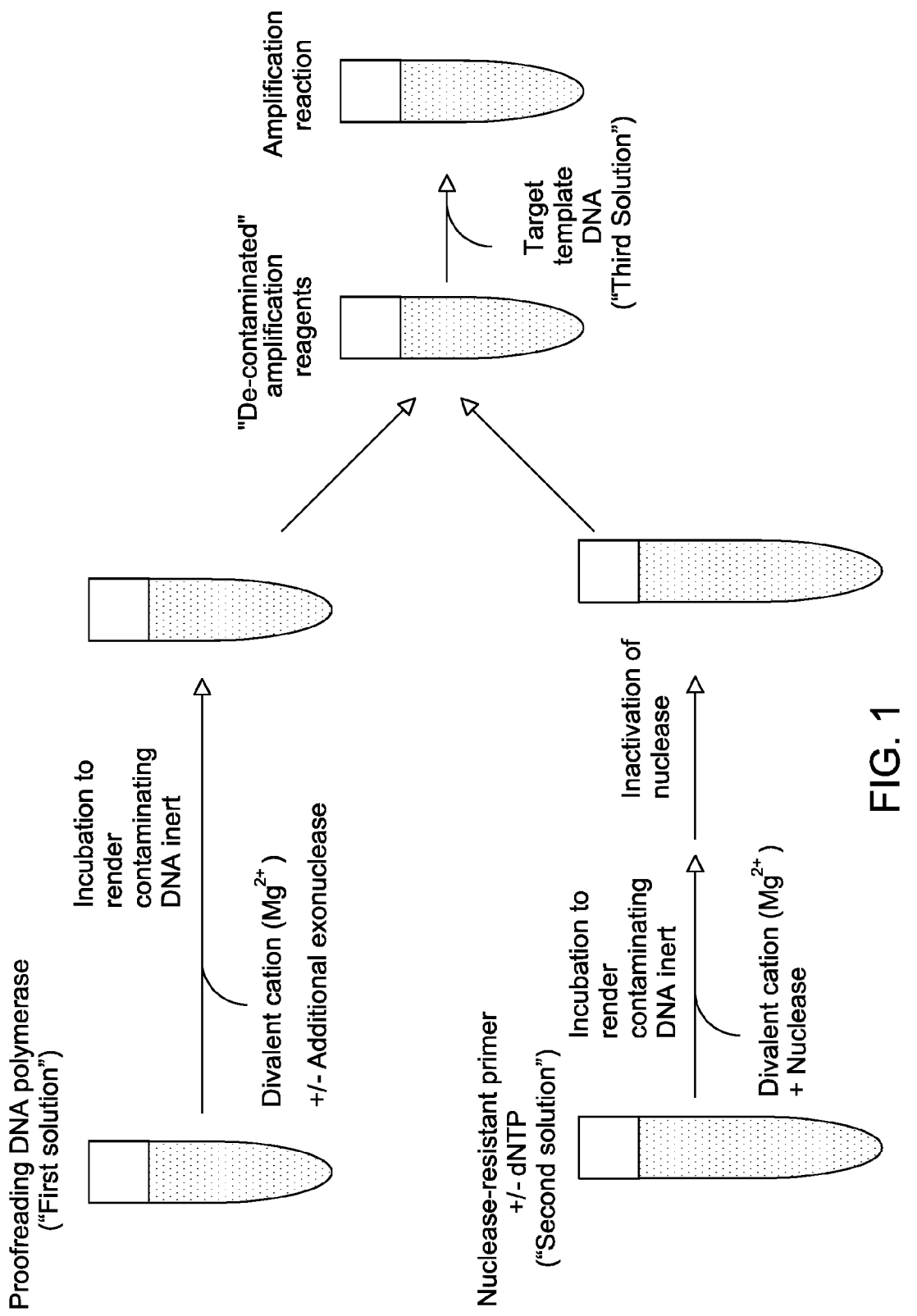
FIG. 1 is a schematic representation of the general embodiment of an amplification reaction of the invention

FIG. 1 is a schematic representation of one of the general embodiments of an amplification reaction of present invention. Contaminating nucleic acids in individual reagents or reagent solutions are rendered inert using the methods in accordance with certain embodiments of the present invention. Figure schematically represents the method for processing of a polymerase solution and a nuclease-resistant primer solution to render the contaminating nucleic acid inert. A proofreading DNA polymerase solution is incubated with a divalent cation in the absence or presence of additional exonucleases to render the contaminating nucleic acid inert. The primer solution is incubated with a nuclease in presence of divalent cations to degrade the contaminating nucleic acid. The primer solution may also contain free nucleotides (dNTPs). The nuclease in the primer solution is then deactivated prior to its use in a subsequent amplification reaction. FIG. 1 also illustrates the use of these de-contaminated reagents or reagent solutions for subsequent reactions such as amplification.

Example 1

Optimization of the exonuclease treatment of a reagent or reagent solution is achieved by analyzing the exonuclease activity in the reagent or reagent solution (buffer solution) used for DNA amplification reaction in comparison with its activity in buffers regularly used in exonuclease treatments. Varying concentrations of a mixture of exonuclease I and exonuclease III (0.25 unit and 1 unit) were incubated with 50 ng of lambda DNA at 37° C. for 1.8 h in presence of 20 mM $MgCl_2$ and 15 mM KCl in different buffer solutions. Some of the buffer solutions used include TempliPhi buffer having 75 mM NaCl (GE Healthcare), 25 mM HEPES (pH=8.0, no salt) and 25 mM HEPES (pH=8.6, no salt). TempliPhi buffer is commonly used in rolling circle amplification reactions. The TempliPhi buffer used included 400 μM of free nucleotides (dNTPs) and 40 μM exonuclease-resistant hexamer primer, NNNN*N*N (*N represents a phosphorothioate modified random nucleotide). The total reaction volume was kept constant at 10 μL. At the end of incubation, the remaining lambda DNA present in the reaction mixture was quantified to understand the exonuclease efficiency in different buffers.

Figure 2:
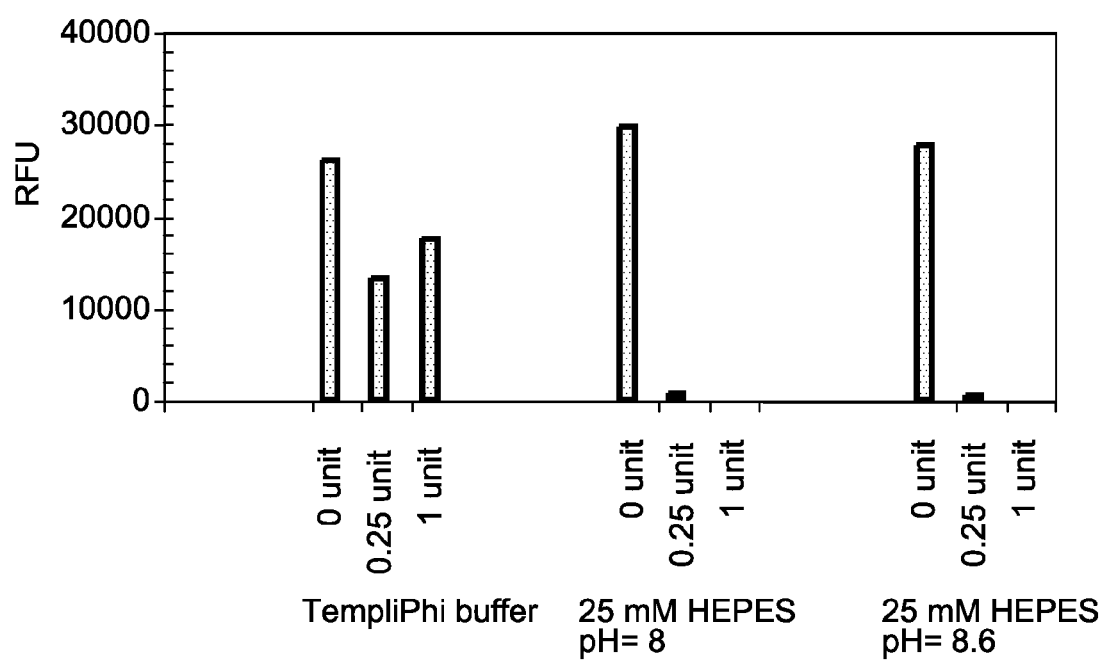
FIG. 2 depicts the exonuclease treatment of reagent/buffer solutions comprising free nucleotides to remove contaminating nucleic acid. Lambda DNA is used as a non-limiting example of a contaminating nucleic acid.

FIG. 2 illustrates the exonuclease treatment of reagent/buffer solutions comprising free nucleotides to remove contaminating nucleic acid. Lambda DNA is used as a non-limiting example of a contaminating nucleic acid. As shown in FIG. 2, the exonuclease was inefficient in digesting the lambda DNA in TempliPhi buffer, whereas complete digestion of the lambda DNA by the exonuclease was achieved in exonuclease buffers (25 mM HEPES, no NaCl) at pH=8.0 and pH=8.6. High salt concentration (>75 mM of NaCl) in TempliPhi buffer inhibited the exonuclease activity. So, in embodiments where high salt (NaCl) concentrations are to be used, the reagents/reagent solutions should be treated with exonuclease prior to the addition of salt solution. The salt (NaCl) solution, in such circumstances, may be separately treated with ultraviolet rays to render any contaminating nucleic acid in the salt solution inert.

Example 2

Use of a proofreading DNA polymerase, either alone or in combination with an exonuclease, to render the contaminating nucleic acid inert is illustrated by the following example. A non-denatured, linear DNA (pUC DNA) was used as a contaminating DNA to illustrate the efficiency of the proofreading DNA polymerase (Phi29 DNA polymerase) to render the contaminating nucleic acid inert. Typically 400 ng of Phi29 DNA polymerase (20 ng/µL) was incubated with 200 ng of pUC DNA in Tris-HCl buffer (50 mM Tris-HCl, pH=8.0, 0.01% Tween-20, 1 mM TCEP) containing 20 mM $MgCl_2$. The incubation was performed at 30° C. for a period of 0 min. to 60 min. The same step was performed with exonuclease III and also with a combination of Phi29 DNA polymerase and exonuclease III. One unit/reaction of exonuclease was used. After the incubation, the concentration of the remaining DNA was estimated by staining the double stranded DNA (ds DNA) with picogreen and quantifying the stain using a Tecan fluorescent plate reader.

Figure 3:
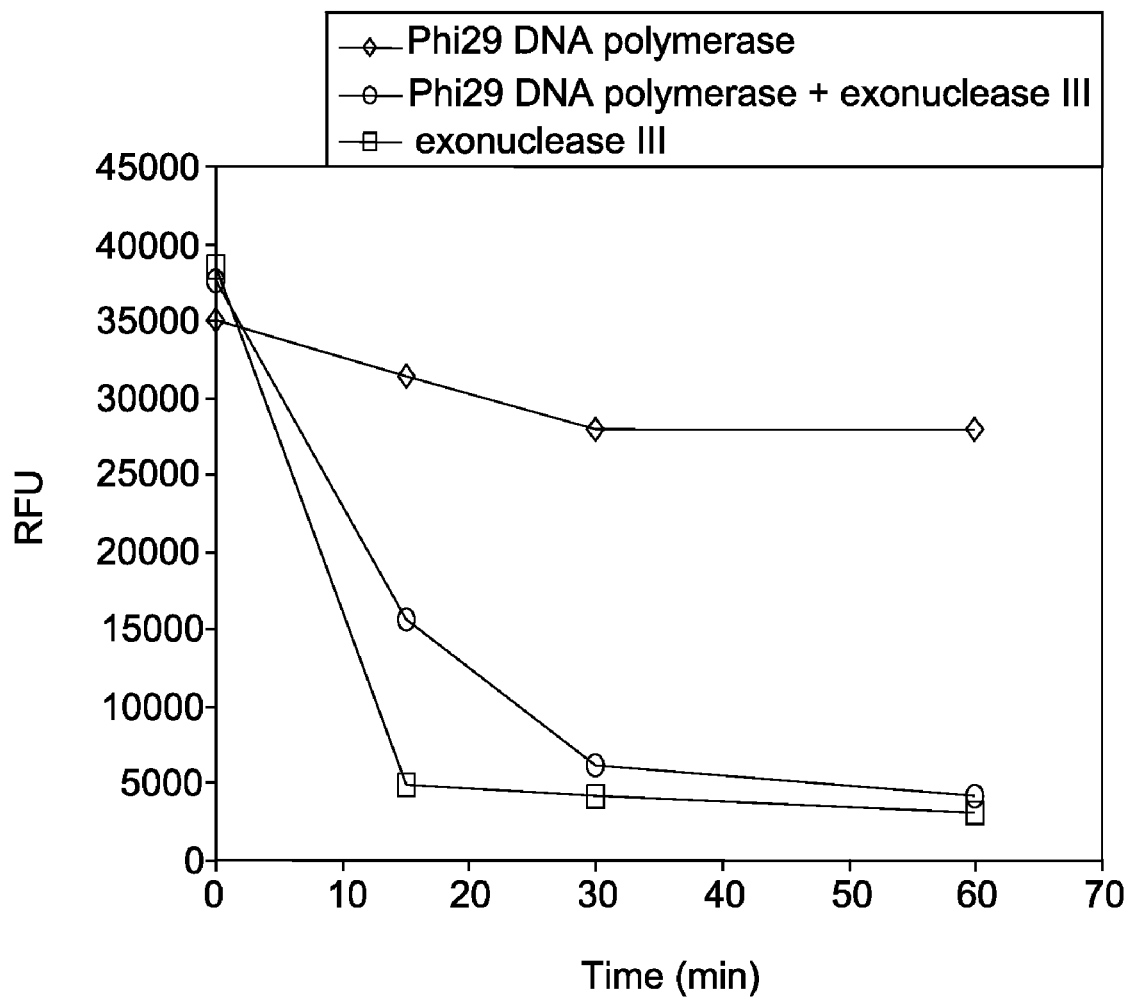
FIG. 3 illustrates an embodiment of the method for processing a polymerase solution over time in which Phi29 polymerase is incubated with a divalent cation to degrade the contaminating nucleic acid.

FIG. 3 illustrates an embodiment of the method for processing a polymerase solution over time in which Phi29 polymerase is incubated with a divalent cation to degrade the contaminating nucleic acid. As shown in FIG. 3, the Phi29 DNA polymerase degraded the pUC DNA upon incubation with magnesium ions. The efficiency of rendering the contaminating DNA inert was greater when the incubation of the Phi29 DNA polymerase was performed along with exonuclease III. FIG. 3 also shows a graph illustrating the effect of exonuclease III treatment on DNA degradation (positive control).

Example 3

Use of an exonuclease to render a contaminating nucleic acid inert in a primer solution is illustrated. A non-denatured, linear DNA (pUC DNA) was used as a contaminating DNA. The primer solution contained an exonuclease-resistant, thioated hexamer primer, NNNN*N*N, having one phosphorothioate linkage between the nucleotides at the terminal 3' position of the primer sequence (*N represents a phosphorothioated random nucleotide). Free nucleotides (dNTPs) were also present in the primer solution during the processing. Typically, a solution of 400 pmoles of the thioated hexamer primer was mixed with 16,000 pmoles of free nucleotides (dNTPs) in 2.5 µL of 2× buffer (50 mM Tris-HCl, pH=8.0, 20 mM $MgCl_2$, 0.01% Tween-20 and 1 mM TCEP) and a mixture of 1 unit of exonuclease 1 and 1 unit of exonuclease III. The solution was then incubated at 37° C. for about 80 min. After the incubation, the concentration of the remaining DNA was estimated by staining the double stranded DNA (ds DNA) with picogreen and quantifying the stain using a Tecan fluorescent plate reader.

Figure 4:
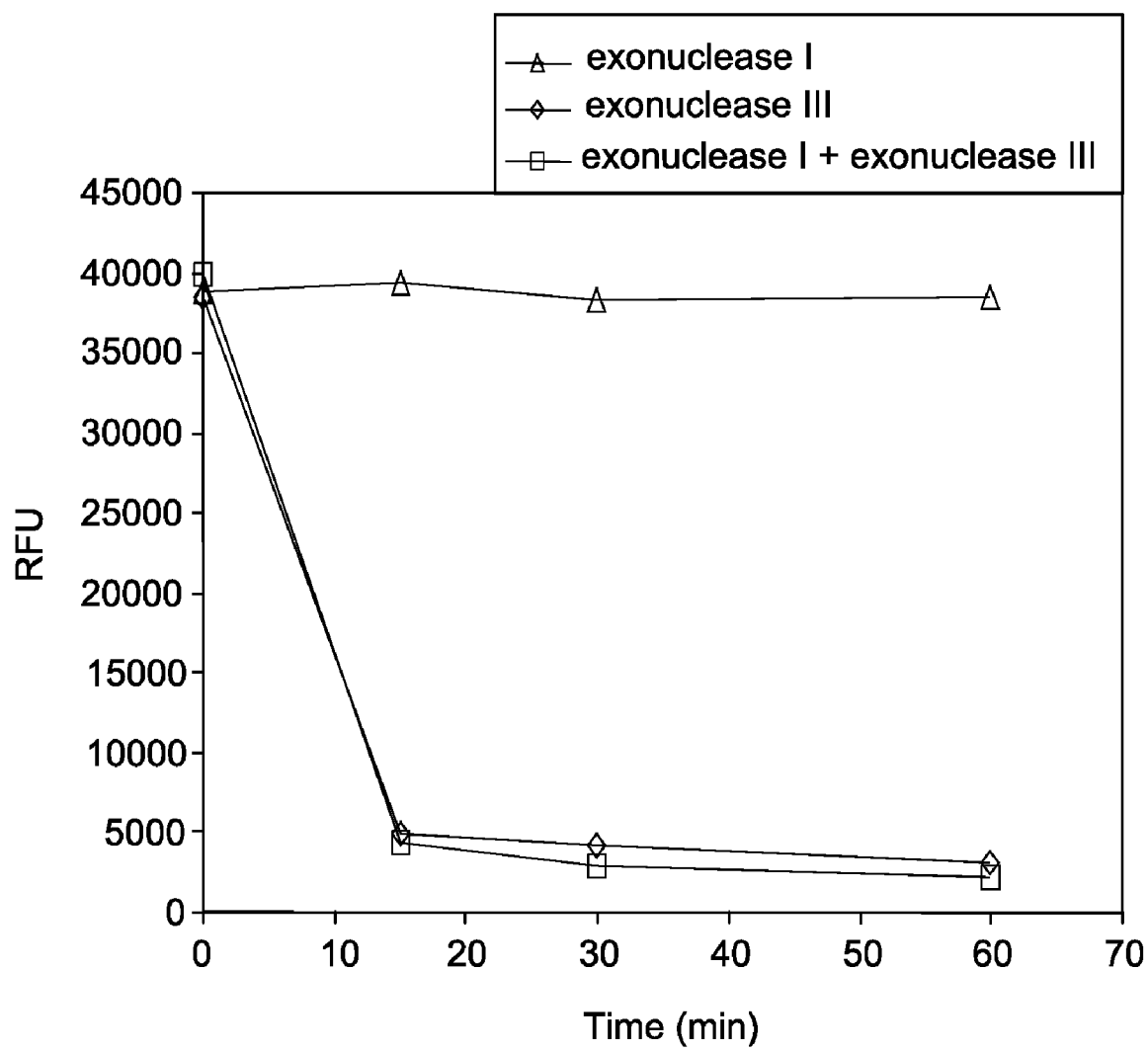
FIG. 4 illustrates an embodiment of the method for processing a primer solution over time using exonuclease I or exonuclease III or a combination of exonuclease I and exonuclease III to degrade the contaminating nucleic acid and render it inert.

FIG. 4 illustrates an embodiment of the method for processing a primer solution over time using exonuclease I or exonuclease III or a combination of exonuclease I and exonuclease III to degrade the contaminating nucleic acid and render it inert. As shown in FIG. 4, the processing of the primer solution by the incubation with the exonucleases and magnesium ions degraded the pUC DNA. Higher efficiencies of de-contamination were observed when a combination of exonuclease III and exonuclease I was used. Use of exonuclease I alone is generally not sufficient to remove the contaminating double stranded DNA.

Example 4

Effect of exonuclease treatment of reagents or reagent solution (primer and proofreading DNA polymerase solutions) on rendering a contaminating nucleic acid inert is illustrated by a DNA amplification reaction in which varying amounts of a target template DNA (DNA to be amplified) is amplified. The DNA amplification was performed using the reagents or the reagent solutions (a primer solution and a proofreading DNA polymerase solution) that are pre-treated or processed with the exonuclease as per one embodiment of the invention. The results were then compared with a control DNA amplification reaction in which the primer solution and the proofreading DNA polymerase solution had not undergone any pre-treatment/process. For processing the polymerase solution lambda exonuclease was used. For processing the primer solution a mixture of exonuclease I and exonuclease III was used.

To render the contaminating nucleic acid inert, the polymerase solution containing 200 ng of Phi29 DNA polymerase was incubated with 1 unit of lambda exonuclease in 5 µL of 1× reaction buffer (50 mM Tris-HCl, pH=8.0) containing 75 mM KCl, 20 mM $MgCl_2$, 0.01% Tween-20 and 1 mM TCEP (Pierce Biotechnology) at 230 for about 80 min. The processed Phi29 DNA polymerase solution was then used for target DNA amplification without prior inactivation of the lambda exonuclease.

An exonuclease-resistant, thioated hexamer primer, NNNN*N*N, having phosphorothioate linkages between the nucleotides at the terminal 3' position of the primer sequence, was selected as a suitable primer for the target template DNA amplification. Approximately 25% of the primer in the primer solution may be sensitive to the exonuclease. Free nucleotides (dNTPs) were also present in the primer solution during the processing. Typically, a solution of 400 pmoles of the thioated hexamer primer was mixed with 16,000 pmoles of free nucleotides (dNTPs) in 2.5 µL of 2× buffer (50 mM Tris-HCl, pH=8.0 containing 75 mM KCl, 20 mM $MgCl_2$, 0.01% Tween-20 and 1 mM TCEP). To this was added a mixture of 1 unit of exonuclease 1 and 1 unit of exonuclease III. The solution was then incubated at 37° C. for about 80 min.

For the positive control DNA amplification reaction, the polymerase solution and the primer solution is treated the same way as described above without adding any exonucleases.

For the amplification of target template DNA, varying concentrations of target template pUC DNA (0 ng, 1 ng, $10^{-2}$ ng, $10^{-4}$ ng, $10^{-6}$ ng, $10^{-8}$ ng) was used. The DNA amplification reaction at 0 ng of target DNA (zero concentration of target DNA) illustrated the false-positives, i.e., amplification of contaminated DNA. In a typical target DNA amplification reaction, 2.5 µL of target DNA in HET (H=10, E=0.1 and T=0.01%) was used with 400 µM of dNTP, 40 µM of thioated primer and 400 ng of Phi29 DNA polymerase (20 ng/µL) in a reaction volume of 20 µL. The same Tris-HCl buffer as mentioned above (50 mM Tris-HCl, pH=8.0 containing 75 mM KCl, 20 mM MgCl$_2$, 0.01% Tween-20 and 1 mM TCEP) was used for the target DNA amplification reaction.

FIG. 5 illustrates the effect of an embodiment of the exonuclease treatment of a primer solution and a polymerase solution on DNA amplification. FIG. 5 and FIG. 6 together illustrate the effect of exonuclease treatment of the primer solution and the proofreading DNA polymerase solution on rolling circle DNA amplification. Primer solution comprising free nucleotides are incubated with a mixture of exonuclease I and exonuclease III along with magnesium ions. Phi29 DNA polymerase is treated with lambda exonuclease. The graphs labeled as "without exonuclease" refers to the control DNA amplification reactions in which no exonuclease pre-treatment/processing was performed. The graphs labeled as "with exonuclease I, exonuclease III, Lambda exonuclease" or "with exonuclease" represent the DNA amplification reactions in which the polymerase or primer solutions have been processed with the exonuclease.

The graphs in FIG. 5 and FIG. 6 show the kinetics of the % yield of amplified DNA with time, with or without the exonuclease treatments. The amount of the target template DNA present in each reaction is indicated in the label of the graph. When the polymerase and the primer solutions are pre-treated/processed with exonuclease, an increase in kinetics of the target DNA amplification was observed. The increased kinetic rates were more prominent when the target template DNA concentrations were above $10^{-6}$ ng. It is possible that at least some of the exonucleases were active for the duration of the target DNA amplification reaction. When the target template DNA concentration was only $10^{-2}$ ng, the exonuclease treatment of either the Phi29 DNA polymerase, the primer solution or the free nucleotide solution did not increase the rate of kinetics of target DNA amplification (FIG. 6)

Example 5

Effect of processing (exonuclease treatment) of reagents or reagent solution on rendering a contaminating nucleic acid inert is illustrated by a real time DNA amplification reaction in which varying amounts of a target template DNA (DNA to be amplified) are amplified. The DNA amplification was performed using the reagents or the reagent solutions (a primer solution and a proofreading DNA polymerase solution) that are pre-treated or processed with the exonuclease as per some embodiments of the invention. The results were then compared with a control DNA amplification reaction in which the primer solution and the proofreading DNA polymerase solution had not undergone any pre-treatment/process. pUC DNA was used as target template DNA. The concentration of the target DNA used ranged from 1 ng to 1 fg pUC DNA was prepared in HET buffer that was filter-sterilized using 0.2µ sterile filter. An exonuclease-resistant, locked nucleic acid primer, NNNN*N*N having phosphorothioate linkages between the nucleotides at the terminal 3' position of the primer sequence was selected as a suitable primer for the reaction. Real-time data was collected in Tecan fluorescent plate reader with 1:10,000 SYBR green in the assay.

To render the contaminating nucleic acid inert, the polymerase solution containing 200 ng of Phi29 DNA polymerase was incubated with 1 unit of exonuclease III in 5 µL of Tris-HCl buffer (pH=8.0) containing 20 mM MgCl$_2$, 0.01% Tween-20 and 1 mM TCEP at 30° C. for about 60 min. The processed Phi29 DNA polymerase solution was then used as such in the target DNA amplification assay without prior inactivation of the exonuclease III.

A solution containing 40 µM of the primer, 400 µM dNTPs and 1:10,000 diluted SYBR green I dye in 50 mM Tris-HCl (50 mM Tris-HCl, pH=8.0, 20 mM MgCl$_2$, 0.01% Tween-20 and 1 mM TCEP) was incubated with 1 unit of exonuclease I and exonuclease III. The solution was then incubated at 30° C. for about 30 min. The exonuclease was then thermally inactivated (by incubating the solution at 85° C. for 15 min followed by an incubation at 95° C. for 5 min.)

For the control DNA amplification reaction, the polymerase solution and the primer solution is treated the same way as described above without adding any exonucleases.

Real-time amplification reaction was performed with varying concentrations of target pUC DNA ($10^8$, $10^6$, $10^4$, $10^2$, or 0 copies of pUC DNA circles). The DNA amplification reaction at 0 ng of target DNA depicted the false-positives, i.e., amplification of contaminated DNA or non-templated DNA amplification.

FIG. 7 illustrates the effect of an embodiment of the step of incubating Phi29 DNA polymerase and a primer solution with an exonuclease on a template DNA titration. It illustrates the effect of exonuclease treatment of the primer solution and the proofreading DNA polymerase solution on real time rolling circle DNA amplification. In this example, pUC DNA is used as a template DNA. The graphs labeled as "without exonuclease cleaned reagents' refers to the control DNA amplification reactions in which no exonuclease pre-treatment/processing was performed. The graphs labeled as "with exonuclease cleaned reagents" represent the DNA amplification reactions in which the polymerase or primer solutions have been processed with the exonuclease. From the graph, it can be observed that, DNA amplification at zero target DNA concentration (the false positives) was considerably reduced when the polymerase solution and the primer solution were processed as per some of the embodiments of the present invention to render the contaminating nucleic acid inert. In this particular reaction, a 50-times reduction in the background false-positive signal (amplification of contaminated nucleic acid) was observed when the reagents or reagent solutions were processed with exonucleases prior to their use in the DNA amplification reaction.

Example 6

Effect of addition of a single stranded DNA binding protein (SSB protein) in the processing of reagents or reagent solution for rendering a contaminating nucleic acid inert as per some embodiments of the present invention is illustrated by a real time DNA amplification reaction. The primer solution used in the DNA amplification reaction was de-contaminated as per some embodiments of the invention by using a combination of exonuclease I, exonuclease III and a single stranded DNA binding protein (SSB protein). The DNA polymerase solution used was also pre-treated or processed with the exonuclease as per some embodiments of the invention. Varying amounts of a target template DNA was then amplified using the processed reagents or reagent solutions. The results were then compared with a control DNA amplification reaction in which the primer solution and the proofreading DNA polymerase solution had not undergone any pre-treatment or process to make the contaminating nucleic acid inert.

Fish DNA was used as target template DNA. The concentration of the target DNA used ranged from 1 ng to 10 fg Fish DNA was prepared in HET buffer that was filter-sterilized using 0.2µ sterile filter. An exonuclease-resistant, locked nucleic acid primer, W+W+N*N*S (+N represents a synthetic, locked random nucleotide, W=A or T, S=G or C) having one phosphorothioate linkage between the nucleotides at the terminal 3' position of the primer sequence was selected as a suitable primer for the reaction. Real-time data was collected in Tecan fluorescent plate reader with 1:10,000 SYBR green in the assay.

As shown in Table 1, to render the contaminating nucleic acid inert, the polymerase solution containing 200 ng of Phi29 DNA polymerase was incubated with 0.1 unit of exonuclease III in 5 µL of 50 mM HEPES buffer (pH=8.0) containing 15 mM KCl, 20 mM MgCl$_2$, 0.01% Tween-20 and 1 mM TCEP. The incubation was performed either at 30° C. for about 60 min. or at 4° C. for 12 h. The processed Phi29 DNA polymerase solution was transferred to an ice-bath and then was used in the target DNA amplification assay without prior inactivation of the exonuclease III.

TABLE 1

Conditions for the de-contamination processing of the DNA polymerase and primer solutions.

| | Primer/Nucleotide Mix (Each reaction) | DNA polymerase (Enzyme) Mix (Each reaction) |
|---|---|---|
| 2X Reaction buffer (Reaction buffer is 50 mM HEPES buffer (pH = 8.0), 15 mM KCl, 20 mM MgCl$_2$, 0.01% Tween-20 and 1 mM TCEP) | 2.5 µL | 2.5 µL |
| Water | — | 2.2 µL |
| 10 mM dNTP mix | 0.4 µL | — |
| 1 mM primer | 0.4 µL | — |
| Exonuclease I (20 unit/µL) | 0.5 µL | — |
| Exonuclease III (10 unit/µL) | 0.1 µL | — |
| Exonuclease III (1 unit/µL) | — | 0.1 µL |
| SSB protein (100 ng/µL) | 1 µL | — |
| 1:100 SYBR Green I | 0.1 µL | — |
| Phi29 DNA polymerase (5 mg/ml) | — | 0.2 µL |
| Total Volume | 5 µL | 5 µL |

To decontaminate the primer solution, it was incubated with a combination of exonuclease I, exonuclease III and SSB protein as shown in Table 1. *E. coli* SSB protein was used in this example for the processing of the primer solution. The primer/nucleotide mix was incubated at 37° C. for about 60 min. The exonuclease was then thermally inactivated by incubating the primer/nucleotide solution at 85° C. for 15 min followed by incubation at 95° C. for 5 min.

For the control DNA amplification reaction, the polymerase solution and the primer solution was treated the same way as described above without adding any exonucleases or SSB protein.

Real-time amplification reaction was then performed with varying concentrations (1 ng to 10 fg of DNA) of target Fish DNA (0 ng, 1 ng, $10^{-10}$ g, $10^{-11}$ g, $10^{-12}$ g, $10^{-13}$ g and $10^{-14}$ g). For DNA amplification, the target DNA was added to the primer/nucleotide mix. Enzyme mix (DNA polymerase mix) was then added to the DNA-primer/nucleotide mix and the DNA amplification reaction was performed for about 260 min. The DNA amplification reaction at 0 ng of target DNA depicted the false-positives, i.e., amplification of contaminated DNA. Composition for the DNA amplification reaction (Total volume 20 µL) included 50 mM HEPES (pH=8.0), 15 mM KCl, 20 mM MgCl$_2$, 0.01% Tween-20, 1 mM TCEP, 400 ng Phi29 DNA polymerase, 2.5 mM TRIS-HCl (pH=7.2), 10 mM NaCl, 0.5 mM DTT, 0.3 mM EDTA, 2.5% (v/v) Glycerol, 0.2 unit exonuclease III, 400 mM dNTP, 800 pm exonuclease-resistant primer (W+W+N*N*S), 2 unit exonuclease III (heat-inactivated), 20 unit exonuclease I (heat-inactivated) and 200 ng *E. coli* SSB protein (heat-inactivated).

FIG. 8, FIG. 9, FIG. 10 and FIG. 11 illustrate the effect of processing of Phi29 DNA polymerase and a primer solution with an exonuclease on the template DNA titration. Figures also illustrate the effect of SSB protein on the exonuclease treatment of the primer solution. As shown in FIG. 8, processing of the nucleotide/hexamer solution eliminated 0.1 pg of DNA to completion using 10 units exonuclease I and one unit exonuclease III. The addition of 100 ng SSB increased the de-contamination efficiency to 10 pg of DNA de-contamination (FIG. 9). As shown in FIG. 10 and FIG. 11, the de-contamination of the Phi29 DNA polymerase eliminated 1 pg to 10 pg of contaminating DNA to completion using 200 ng of Phi29 DNA polymerase and 0.1 unit exonuclease III.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

What is claimed is:

1. A method for decontaminating a proofreading DNA polymerase, comprising the steps of:
   (a) providing a polymerase solution consisting essentially of the proofreading DNA polymerase that is contaminated with a contaminating nucleic acid;
   (b) contacting the polymerase solution with a divalent cation to form a polymerase-cation mixture; and
   (c) incubating the polymerase-cation mixture whereby the contaminating nucleic acid is rendered inert by the proofreading DNA polymerase,
   wherein the contacting and the incubating steps are performed in the absence any substantial amount of free nucleotides (dNTPs), and wherein the decontamination is performed in the absence of an exonuclease or DNAse.

2. The method of claim 1, wherein the proofreading DNA polymerase is a Phi29 DNA polymerase.

3. A method for decontaminating a nuclease-resistant primer solution comprising the steps of:
   (a) providing the primer solution consisting of the nuclease-resistant primer and a contaminating nucleic acid;
   (b) contacting the primer solution with a nuclease and a divalent cation; and
   (c) incubating the primer solution whereby the contaminating nucleic acid is rendered inert by the nuclease.

4. The method of claim 3, wherein the nuclease is selected from the group consisting of exonuclease I, exonuclease III and combinations thereof.

5. The method of claim 3, further comprising steps of inactivating the nuclease, adding a DNA polymerase, adding a DNA template, adding free nucleotides (dNTPs); and amplifying the DNA template.

6. The method of claim 5, wherein the DNA polymerase comprises a Phi29 DNA polymerase.

7. A method to amplify a target DNA comprising the steps of:
   (a) incubating a first solution with a first divalent cation to render a first contaminating nucleic acid inert, wherein the first solution consists essentially of a proofreading DNA polymerase that is contaminated with the first contaminating nucleic acid, wherein the first solution does not contain any substantial amount of free nucleotides (dNTPs), and wherein the incubation of the first solution is performed in the absence of an exonculease or DNAse;

(b) incubating a second solution with an exonuclease and a second divalent cation to render a second contaminating nucleic acid inert, wherein the second solution consists of a nuclease resistant primer and the second contaminating nucleic acid;

(c) inactivating the exonuclease in the second solution;

(d) mixing the first solution and the second solution with a third solution comprising the target DNA; and (e) amplifying the target DNA.

8. The method of claim 7, wherein the proofreading DNA polymerase is a Phi29 DNA polymerase.

9. The method of claim 7, wherein the exonuclease is a mixture of exonuclease I and exonuclease III.

10. The method of claim 7, wherein the target DNA is amplified using a DNA amplification method selected from the group consisting of rolling circle amplification, strand displacement amplification and multiple displacement amplification.

11. The method of claim 1, wherein the contaminating nucleic acid is a double-stranded deoxry ribonucleic acid.

12. The method of claim 1, wherein the polymerase solution further consists essentially of a non-proofreading DNA polymerase.

13. A method for decontaminating a proofreading DNA polymerase that is contaminated with a contaminating DNA, the method comprising;

incubating the proofreading DNA polymerase with a divalent cation in the absence of any substantial amount of free nucleotides, wherein the decontamination is performed in the absence of any exonuclease or DNAse.

14. A method for decontaminating a proofreading DNA polymerase consisting the steps of:

(a) providing a polymerase solution consisting of the proofreading DNA polymerase that is contaminated with a contaminating nucleic acid;

(b) contacting the polymerase solution with a divalent cation to form a polymerase-cation mixture; and (c) incubating the polymerase-cation mixture whereby the proofreading DNA polymerase degrades the contaminating nucleic acid.

15. The method of claim 14, wherein the proofreading DNA polymerase is a Phi29 DNA polymerase.

16. The method of claim 14, wherein the divalent cation is $Mg^{2+}$ ion.

* * * * *